United States Patent
Chen et al.

(10) Patent No.: US 11,524,955 B2
(45) Date of Patent: *Dec. 13, 2022

(54) 2,4-DIAMINO-PYRIMIDINE COMPOUNDS AND METHOD FOR MAKING AND USING THE COMPOUNDS

(71) Applicant: Rigel Pharmaceuticals, Inc., South San Francisco, CA (US)

(72) Inventors: Yan Chen, Foster City, CA (US); Rose Yen, San Francisco, CA (US); Jiaxin Yu, Foster City, CA (US); Vanessa Taylor, San Francisco, CA (US); Rajinder Singh, Belmont, CA (US)

(73) Assignee: Rigel Pharmaceuticals, Inc., South San Francisco, CA (US)

(*) Notice: Subject to any disclaimer, the term of this patent is extended or adjusted under 35 U.S.C. 154(b) by 18 days.

This patent is subject to a terminal disclaimer.

(21) Appl. No.: 16/893,981

(22) Filed: Jun. 5, 2020

(65) Prior Publication Data

US 2020/0299276 A1 Sep. 24, 2020

Related U.S. Application Data

(63) Continuation of application No. 15/633,258, filed on Jun. 26, 2017, now Pat. No. 10,710,983.

(60) Provisional application No. 62/355,189, filed on Jun. 27, 2016.

(51) Int. Cl.
| | | |
|---|---|---|
| *C07D 239/48* | (2006.01) | |
| *C07D 403/12* | (2006.01) | |
| *C07D 401/14* | (2006.01) | |
| *C07D 405/14* | (2006.01) | |

(52) U.S. Cl.
CPC ......... *C07D 403/12* (2013.01); *C07D 239/48* (2013.01); *C07D 401/14* (2013.01); *C07D 405/14* (2013.01)

(58) Field of Classification Search
CPC .. C07D 239/48; C07D 401/12; C07D 401/14; C07D 403/12; C07D 403/14; A61K 31/505; A61K 31/506
USPC .......................... 544/323, 324, 325; 514/275
See application file for complete search history.

(56) References Cited

U.S. PATENT DOCUMENTS

| | | |
|---|---|---|
| 4,738,851 A | 4/1988 | Schoenwald et al. |
| 4,882,150 A | 11/1989 | Kaufman |
| 4,921,475 A | 5/1990 | Sibalis |
| 5,008,110 A | 4/1991 | Benecke et al. |
| 5,077,033 A | 12/1991 | Viegas et al. |
| 5,087,240 A | 2/1992 | Sibalis |
| 5,088,977 A | 2/1992 | Sibalis |
| 5,163,899 A | 11/1992 | Sibalis |
| 5,164,189 A | 11/1992 | Eh et al. |
| 5,254,346 A | 10/1993 | Tucker et al. |
| 5,290,561 A | 3/1994 | Eh et al. |
| 5,336,168 A | 8/1994 | Sibalis |
| 5,352,456 A | 10/1994 | Fallon et al. |
| 5,403,841 A | 4/1995 | Lang et al. |
| 5,521,222 A | 5/1996 | Ali et al. |
| 5,698,219 A | 12/1997 | Valdivia et al. |
| 5,776,445 A | 7/1998 | Cohen et al. |
| 5,800,807 A | 9/1998 | Hu et al. |
| 6,056,950 A | 5/2000 | Saettone et al. |

(Continued)

FOREIGN PATENT DOCUMENTS

| | | |
|---|---|---|
| CN | 105017159 | 11/2015 |
| JP | 2008-544972 | 12/2008 |

(Continued)

OTHER PUBLICATIONS

Powell et al., Optimization of highly selective 2,4-diaminopyrimidine-5-carboxamide inhibitors of Sky kinase, Bioorganic & Medicinal Chemistry Letters, 23 (2013), pp. 1051-1055.*

(Continued)

*Primary Examiner* — Deepak R Rao
(74) *Attorney, Agent, or Firm* — Klarquist Sparkman, LLP

(57) ABSTRACT

Compounds within the scope of the present invention have a Formula 1

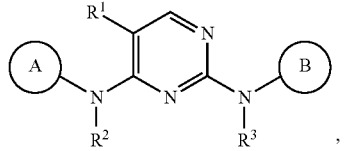

Formula 1 or a salt or produg thereof, where ring A is selected from cycloaliphatic; ring B is aryl; $R^1$ is selected from (C1-C10) alkyl, (C3-C10)cycloalkyl, halo, aryl, and heteroaryl; and $R^2$ and $R^3$ are independently selected from hydrogen and (C1-C6)alkyl. Disclosed compounds may have an IRAK4 $IC_{50}$ of from 0.003 μM to 3.7 μM; a TAK1 $IC_{50}$ of from 0.008 μM to 132 μM; and/or an IRAK4/TAK1 selectivity of from 1 to 450. Particular compounds may have an IRAK4/TAK1 selectivity of from 100 to 500. Disclosed compositions may be formulated as pharmaceutical compositions. A method for using the compounds and/or compositions also are disclosed. The method may comprise administering to a subject an effective amount of a compound within the scope of the present invention, particularly to selectively inhibit IRAK 1 and/or IRAK4 over TAK1.

18 Claims, 7 Drawing Sheets

(56) References Cited

U.S. PATENT DOCUMENTS

| | | | |
|---|---|---|---|
| 6,197,934 | B1 | 3/2001 | DeVore et al. |
| 6,261,547 | B1 | 7/2001 | Bawa et al. |
| 7,754,714 | B2* | 7/2010 | Li .................... A61P 15/00 |
| | | | 514/235.8 |
| 8,993,585 | B2 | 3/2015 | Singh et al. |
| 10,710,983 | B2* | 7/2020 | Chen .................... A61P 25/00 |
| 2007/0032514 | A1 | 2/2007 | Zahn et al. |
| 2007/0232632 | A1* | 10/2007 | Lucking .................... A61P 1/04 |
| | | | 514/275 |
| 2008/0153815 | A1 | 6/2008 | Singh et al. |
| 2010/0081679 | A1 | 4/2010 | Greul et al. |
| 2010/0137313 | A1* | 6/2010 | Boriack-Sjodin .... C07D 471/04 |
| | | | 544/122 |
| 2011/0245242 | A1 | 10/2011 | Greul et al. |
| 2015/0038481 | A1 | 2/2015 | Wang et al. |
| 2015/0259328 | A1 | 9/2015 | Bauer et al. |

FOREIGN PATENT DOCUMENTS

| | | |
|---|---|---|
| JP | 2011-518219 | 6/2011 |
| JP | 2012-528121 | 11/2012 |
| JP | 2015-501810 | 1/2015 |
| JP | 2015-51754 | 6/2015 |
| JP | 2012-501978 | 1/2021 |
| WO | WO 2006/055561 | 5/2006 |
| WO | WO 2009/131687 | 10/2009 |
| WO | WO 2010/136559 | 12/2010 |
| WO | WO 2013/054351 | 4/2013 |
| WO | WO 2013/079494 | 6/2013 |
| WO | WO 2013/177168 | 11/2013 |
| WO | WO 2014/058685 | 4/2014 |
| WO | WO 2014/058921 | 4/2014 |
| WO | WO 2015/157127 | 10/2015 |

OTHER PUBLICATIONS

Seganish et al., "Discovery and Structure Enabled Synthesis of 2,6-Diaminopyrimidin-4-one IRAK4 Inhibitors," *ACS Medicinal Chemistry Letters* 6:942-947, 2015.
Foster, "The Pathophysiology of Ocular Allergy: Current Thinking," *Allergy* 50(21 Suppl):6-9, 1995.
Hanks et al., "Protein Kinases 6. The eukaryotic protein kinase superfamily: kinase (catalytic) domain structure and classification," *The FASEB Journal* 9(8):576-596, 1995.
Kawaguchi et al., "Nasal mast cells in experimentally induced allergic rhinitis in guinea-pigs," *Clin. Exp. Allergy* 24(3):23 8-244, 1994.
Sugimoto et al., "A new model of allergic rhinitis in rats by topical sensitization and evaluation of $H_1$-receptor antagonists," *Immunopharmacology* 48(1):1-7, 2000.
Szelenyi et al., "Animal Models of Allergic Rhinitis," *Arzneimittelforschung* 50(11):1037-1042, 2000.
Tumas et al., "Anti-IgE efficacy in murine asthma models is dependent on the method of allergen sensitization," *J. Allergy Clin. Immunol.* 107(6): 1025-1033, Jun. 2001.
Zhou et al., "Interaction-Site Prediction for Protein Complexes: a Critical Assessment," *Bioinformatics* 23(17):2203-2209, 2007.

\* cited by examiner

2,4-DIAMINO-PYRIMIDINE COMPOUNDS AND METHOD FOR MAKING AND USING THE COMPOUNDS

CROSS REFERENCE TO RELATED APPLICATION

This application is a continuation of U.S. application Ser. No. 15/633,258, filed on Jun. 26, 2017, which in turn claims the benefit of U.S. provisional patent application No. 62/355,189, filed on Jun. 27, 2016. Both of these prior applications are incorporated herein by reference in their entireties.

FIELD

This disclosure concerns 2,4-diamino-pyrimidine compounds, particularly 5-aryl-2,4-diamino-pyrimidine compounds, and embodiments of a method for making and using the compounds, such as for inhibiting interleukin receptor-associated kinase (IRAK), and for treating diseases and conditions related to IRAK.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Certain compounds within the scope of the present invention have a Formula 1

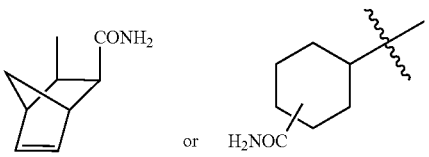

Formula 1 or a salt or produg thereof. With reference to Formula 1, ring A is selected from cycloaliphatic, such as (C6-C12) cycloalkyl, (C6-C12) cycloalkenyl, (C6-C12) bicycloalkyl and (C6-C12) bicycloalkenyl; Ring B is selected from aryl and heteroaryl; $R^1$ is selected from (C1-C10)alkyl, (C3-C10) cycloalkyl, halo, aryl, and heteroaryl, most typically aryl and heteroaryl; and $R^2$ and $R^3$ are independently selected from hydrogen and (C1-C6)alkyl, particularly methyl.

For particular embodiments, the A ring was selected from

and

Certain disclosed embodiments concern compounds comprising substituted A rings, particularly substituted (C6-C12) cycloalkyl, (C6-C12) cycloalkenyl, (C6-C12) bicycloalkyl or (C6-C12) bicycloalkenyl rings, even more particularly carboxamide-substituted (C6-C12) cycloalkyl, (C6-C12) cycloalkenyl, (C6-C12) bicycloalkyl or (C6-C12) bicycloalkenyl rings, such as an A ring selected from

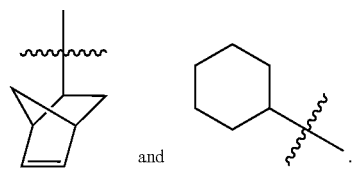 [SMILES: *C1CC2C=CC1C2 ; *C1CCCCC1]

The B ring also may be a substituted ring, such as a mono-, di-, or tri-substituted ring, particularly a mono-, di- or tri-substituted phenyl ring. Certain embodiments concern compounds comprising a B ring substituted with a (C1-10) amide, a (C3-C10)cycloamide, a (C1-C10)alkyl group, such as methyl, a (C1-C10)alkoxyl group, a (C3-C10)cycloalkoxyl group, a halogen, such as fluoro, a (C3-C10) cycloalkyl group, or a (C3-C10)heterocycloalkyl group.

For certain disclosed embodiments, $R^1$ is methyl, cyclopropyl, fluoro, phenyl, pyridyl or furanyl, particularly phenyl, substituted phenyl, pyridyl, substituted pyridyl, furanyl or substituted furanyl, such as halophenyl, halopyridyl, cyanophenyl or cyanopyridyl. For particular embodiments, $R^1$ is $CH_3$,

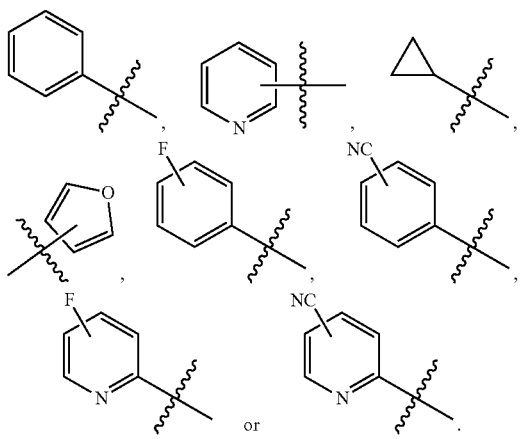

Compounds within the scope of the present invention also may satisfy one or more of the formulas shown below, wherein the A ring, the B ring, $R^1$, $R^2$ and $R^3$ are as appropriate for each of such formulas as previously stated concerning Formula 1.

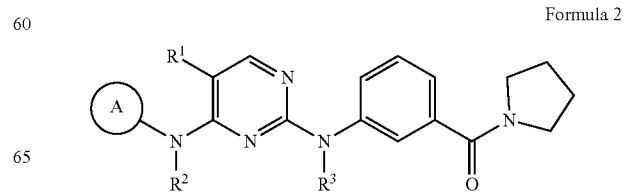

Formula 2

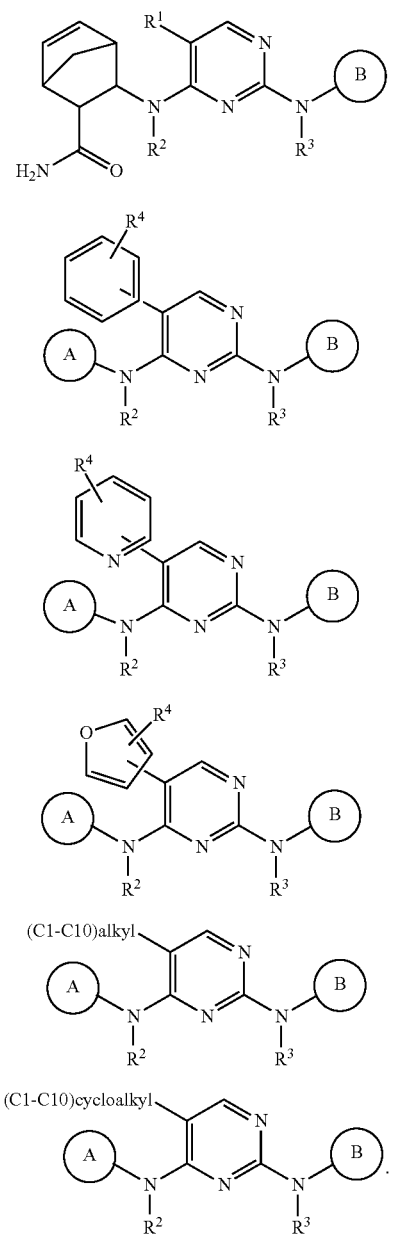

Formula 3

Formula 4

Formula 5

Formula 6

Formula 16

Formula 20

With reference to Formulas 4-6, $R^4$ is selected from (C1-C6)alkyl, particularly methyl, cyano, halo, particularly fluoro, and hydrogen.

Compounds of the present disclosure have an IRAK4 $IC_{50}$ of from 0.003 μM to 3.7 μM; a TAK1 $IC_{50}$ of from 0.008 μM to 132 μM; and an IRAK4/TAK1 selectivity of from 1 to 450. Particular compounds are 5-aryl-substituted pyrimidinediamines having an IRAK4/TAK1 selectivity of from 100 to 500, more particularly halophenyl-substituted pyrimidinediamines having an IRAK4/TAK1 selectivity of greater than 400 or cyanophenyl-substituted pyrimidinediamines having an IRAK4/TAK1 selectivity of greater than 150.

Compositions comprising compounds within the scope of the present invention and a pharmaceutically acceptable excipient also are disclosed. Such compositions may also include at least one additional therapeutic.

One disclosed embodiment of method for using the compounds comprises inhibiting a protein, particularly an IRAK and/or TAK protein, particularly IRAK1, IRAK4, TAK1, and combinations thereof, comprising contacting the protein, either ex vivo, in vivo, or in vitro, with an effective amount of a compound within the scope of the present invention. The method may comprise administering to a subject an effective amount of a compound within the scope of the present invention, particularly administering a compound to a subject to selectively inhibit at least one of IRAK1 and IRAK4 over TAK1, as disclosed 5-aryl-substituted pyrimidinediamines typically have an IRAK4/TAK1 selectivity of from 100 to 500. Disclosed halophenyl-substituted pyrimidinediamines, for example, have an IRAK4/TAK1 selectivity of greater than 400, and cyanophenyl-substituted pyrimidinediamines have an IRAK4/TAK1 selectivity of greater than 150.

DRAWINGS

Figure 1:
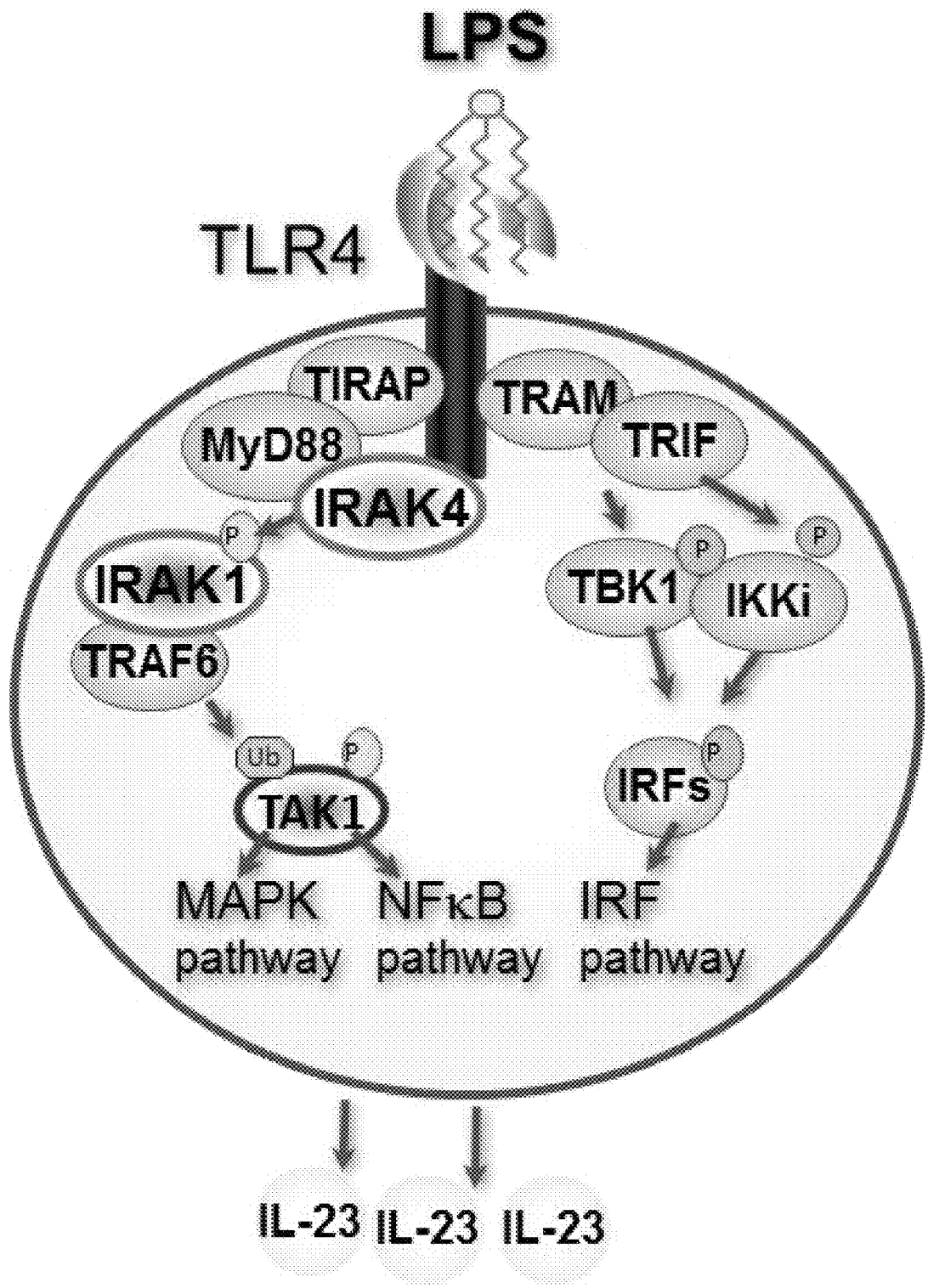
FIG. 1 is a schematic diagram illustrating a rationale for a primary cell-based assay comprising blocking IL-23 by inhibition of IRAK1/4.
Figure 2:
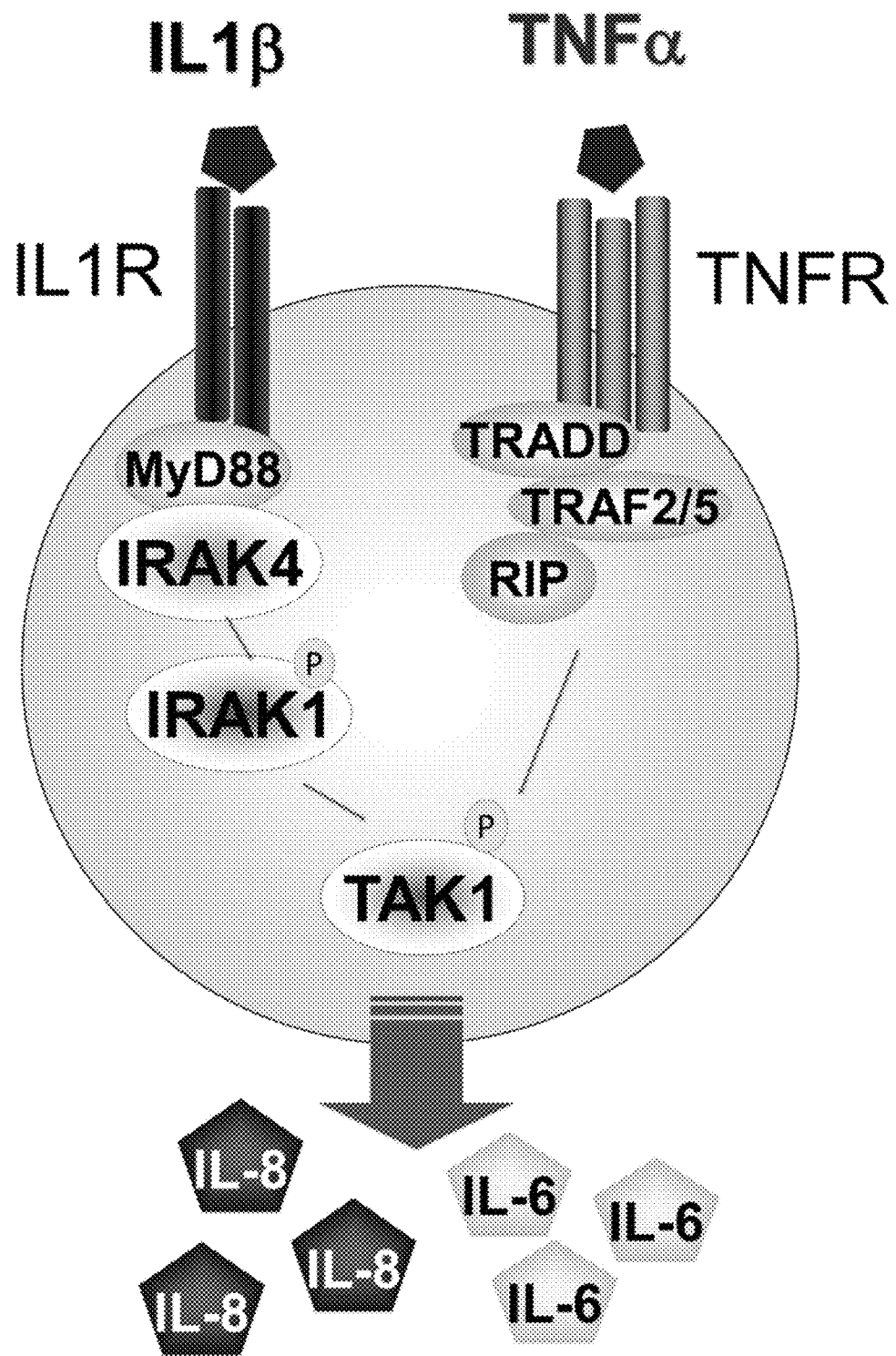
FIG. 2 is a schematic diagram illustrating cell-based assay for TAK1 selectivity where TAK1 is common to both IL1R and TNFR signaling, and IRAK1/4 are not.
Figure 3:
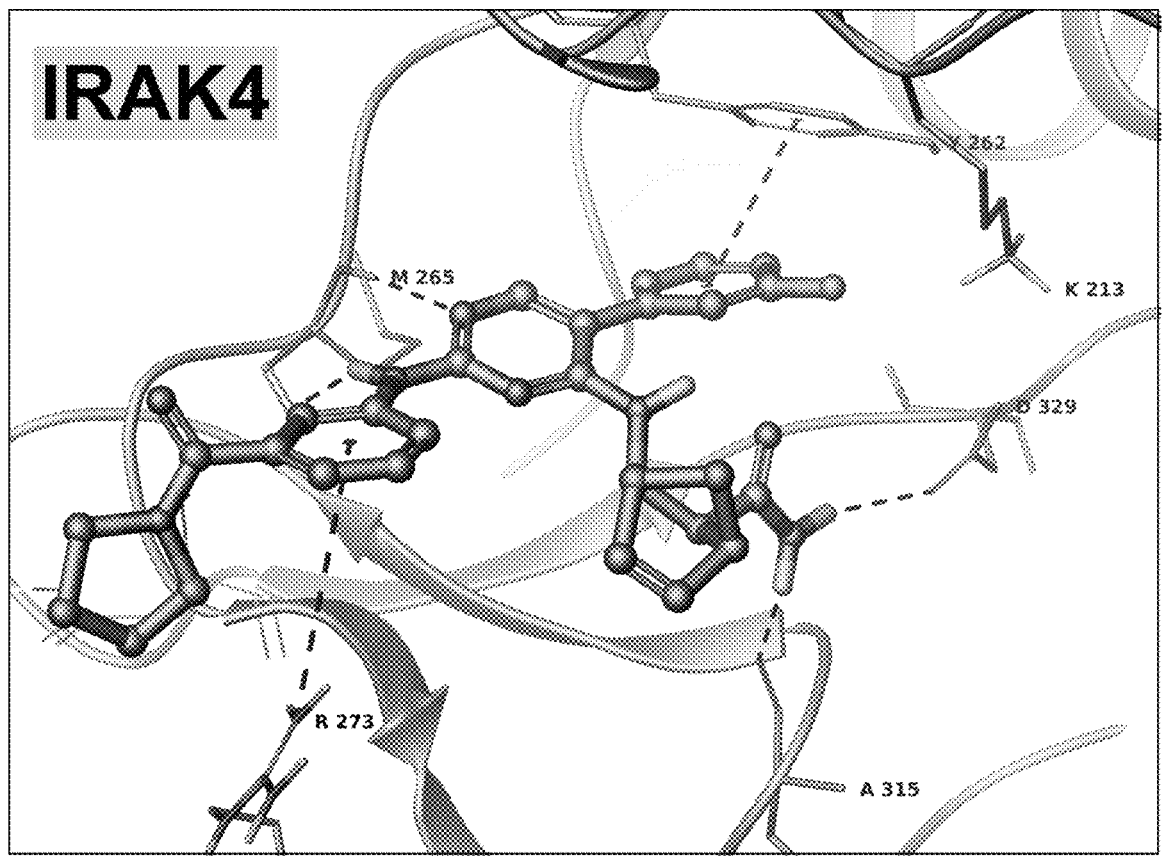
FIG. 3 is a crystal structure of IRAK4 illustrating binding of an exemplary compound according to the present invention.
Figure 3:
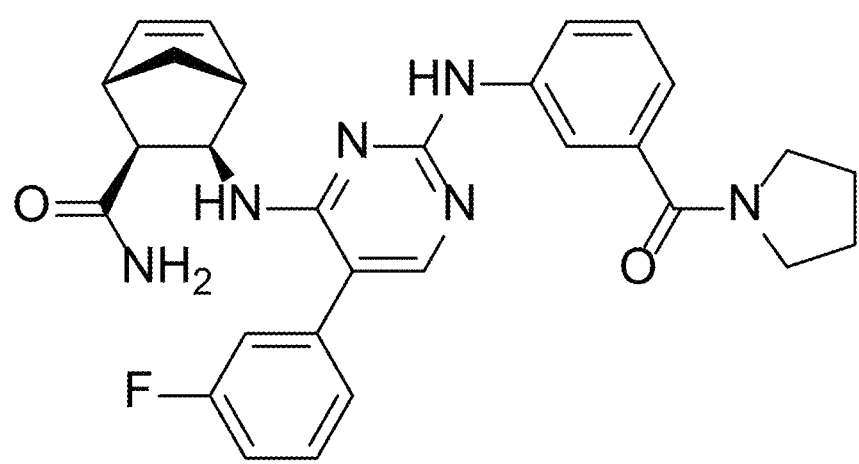
Figure 4:
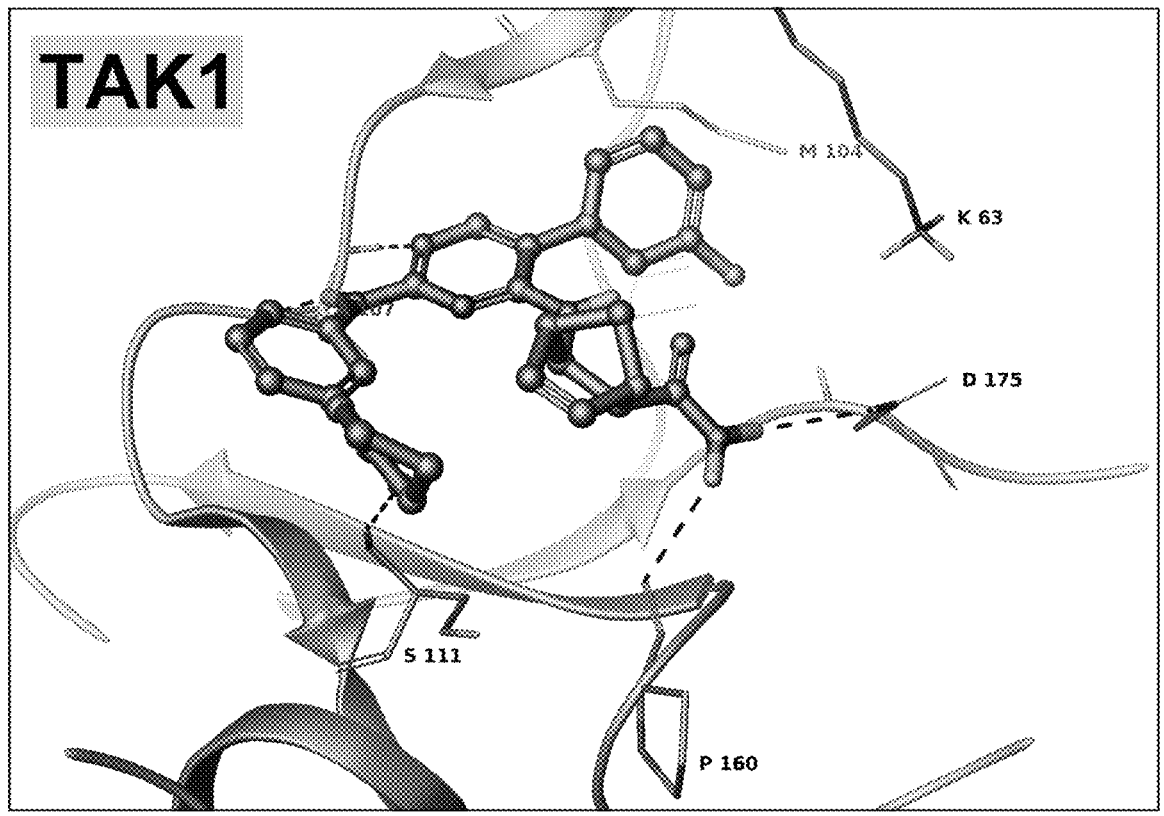
FIG. 4 is a crystal structure of TAK1 illustrating binding of an exemplary compound according to the present invention.
Figure 4:
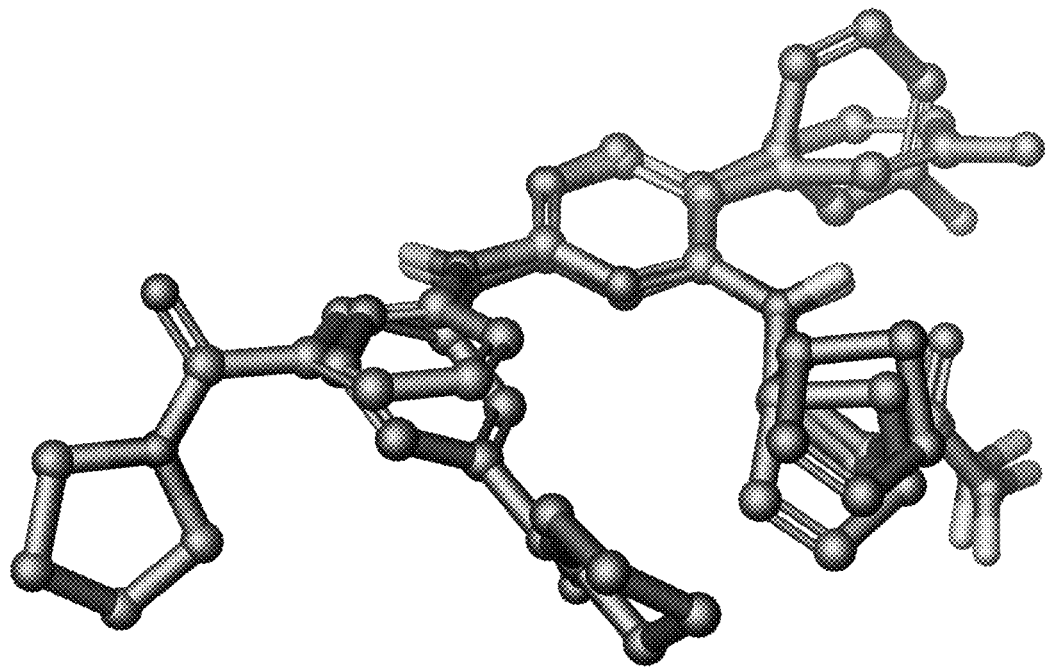
Figure 5:
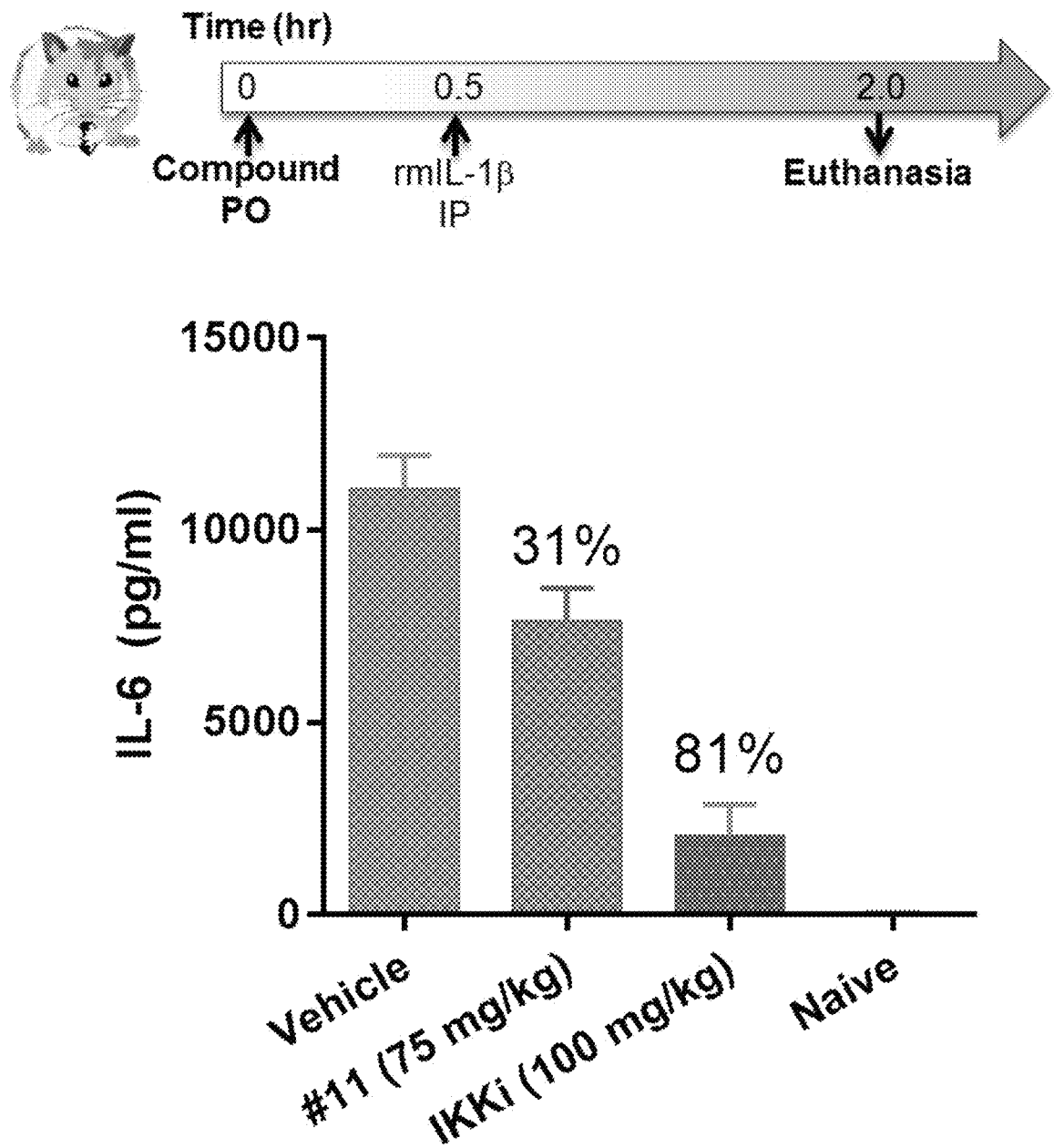
Figure 5A:
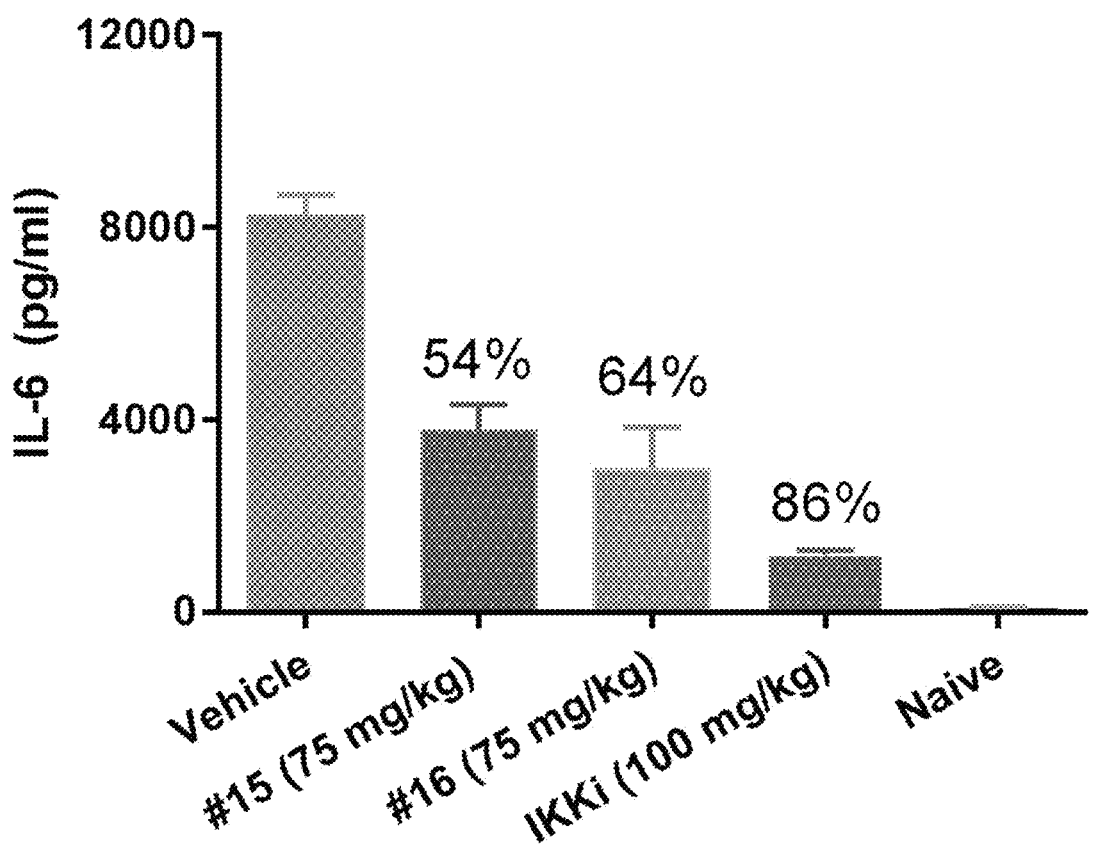

FIGS. 5 and 5A concern an acute mouse model illustrating inhibition of IL-6 induced by IL-1β, as well as results obtained using certain exemplary compounds according to the present invention.

Figure 6:
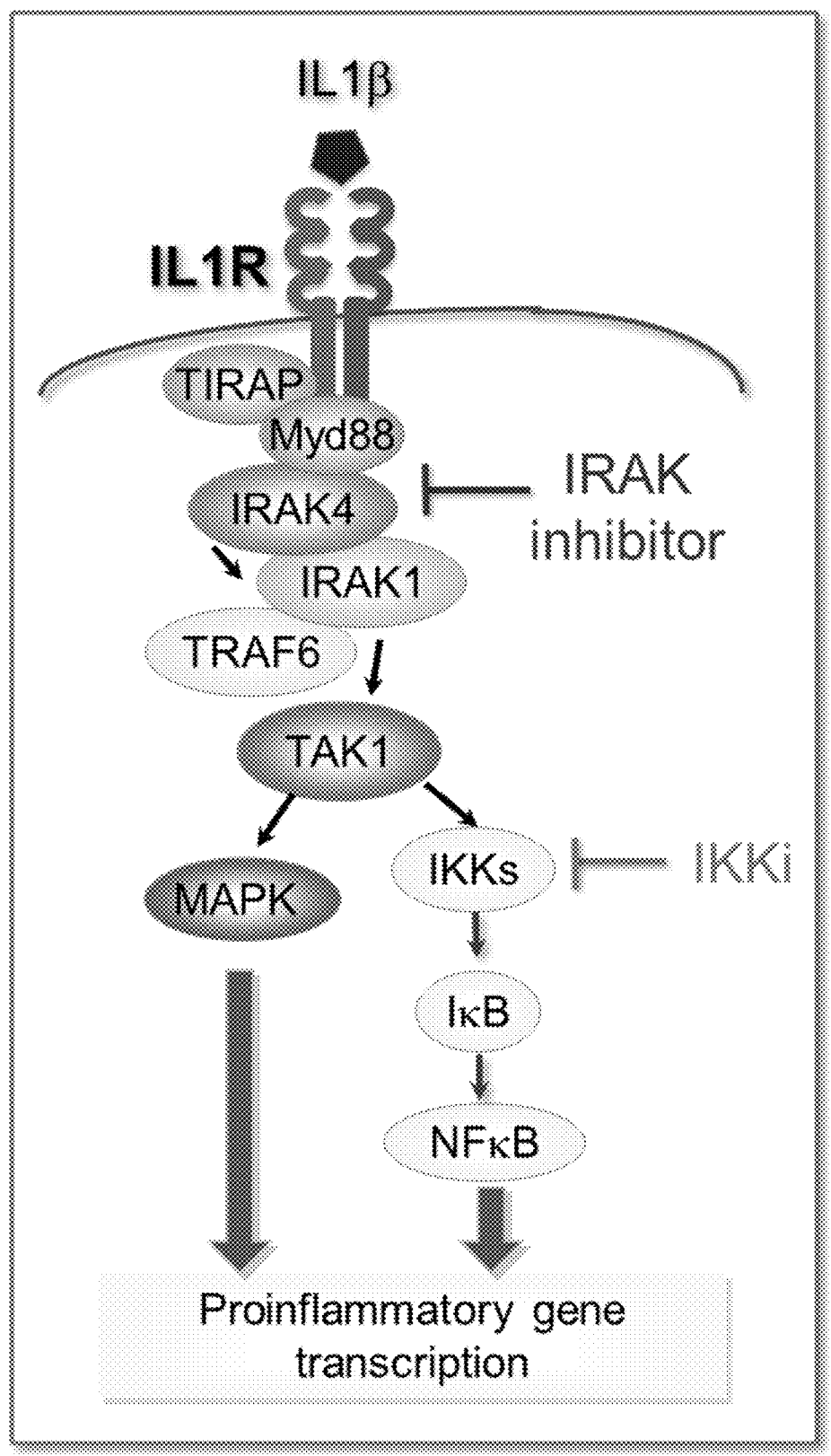

FIG. 6 is a schematic diagram illustrating using an IRAK inhibitor to inhibit a proinflammatory gene transcription pathway.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

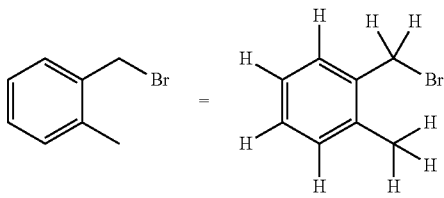

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

A person of ordinary skill in the art will appreciate that the definitions may be combined to further describe a particular compound. For example, hydroxyaliphatic refers to an aliphatic group substituted with an hydroxy (—OH) group, and haloalkylaryl refers to an aryl group substituted with an alkyl group, where the alkyl group too is substituted with a halogen.

Certain disclosed formulas may include one or more "floating" groups to indicate variable positioning of the R group, as for example with the formulae

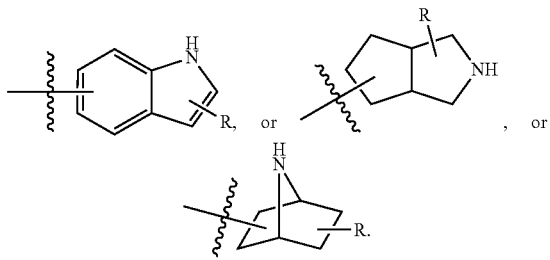

Unless otherwise specified, the "floating" groups may be attached to any atoms of the ring system by replacing a depicted, implied, or expressly defined hydrogen on the ring system, as long as a chemically stable compound results form the attachment.

As used herein, the term "substituted" refers to all subsequent modifiers in a term, for example in the term "substituted arylC$_{1-8}$alkyl," substitution may occur on the "C$_{1-8}$alkyl" portion, the "aryl" portion or both portions of the arylC$_{1-8}$alkyl group. Also by way of example, alkyl includes substituted cycloalkyl groups.

"Substituted," when used to modify a specified group or moiety, means that at least one, and perhaps two or more, hydrogen atoms of the specified group or moiety is independently replaced with a substituent or a substituent group, with exemplary substitutent being defined below. A group, moiety or substituent may be substituted or unsubstituted, unless context indicates otherwise or unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" substituent may be unsubstituted or substituted, but an "unsubstituted alkyl" may not be substituted.

"Substituents" or "substituent groups" for substituting for one or more hydrogen atoms on saturated carbon atoms in the specified group or moiety are, unless otherwise specified, —R$^{60}$, halo, =O, —OR$^{70}$, —SR$^{70}$, —N(R$^{80}$)$_2$, haloalkyl, perhaloalkyl, —CN, —NO$_2$, =N$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —P(O)(O$^-$)$_2$(M$^+$)$_2$, —P(O)(O$^-$)$_2$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$, M$^+$, —CO$_2$R$^{70}$, —C(S)OR$^{70}$, —C(O)N(R$^{80}$)$_2$, —C(NR$^{70}$)(R$^{80}$)$_2$, —OC(O)R$^{70}$, —OC(S) R$^{70}$, —OCO$_2^-$M$^+$, —OCO$_2$R$^{70}$, —OC(S)OR$^{70}$, —NR$^{70}$C (O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$ is C$_{1-6}$alkyl optionally substituted with 1, 2, or 3 OH; each R$^{70}$ is independently for each occurrence hydrogen or R$^{60}$; each R$^{80}$ is independently for each occurrence R$^{70}$ or alternatively, two R$^{80}$ groups, taken together with the nitrogen atom to which they are bonded, form a 3- to 7-membered heteroalicyclyl which optionally includes from 1 to 4 of the same or different additional heteroatoms selected from O, N and S, of which N optionally has H or C$_1$-C$_3$alkyl substitution; and each M$^+$ is a counter ion with a net single positive charge. Each M$^+$ is independently for each occurrence, for example, an alkali metal ion, such as K$^+$, Na$^+$, Li$^+$; an ammonium ion, such as $^+$N(R$^{60}$)$_4$; a protonated amino acid ion, such as a lysine ion, or an arginine ion; or an alkaline metal earth ion, such as [Ca$^{2+}$]$_{0.5}$, [Mg$^{2+}$]$_{0.5}$, or [Ba$^{2+}$]$_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —N(R$^{80}$)$_2$ includes —NH$_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon can be replaced with =O, =NR$^{70}$, =N—OR$^{70}$, =N$_2$ or =S.

Substituent groups for replacing hydrogen atoms on unsaturated carbon atoms in groups containing unsaturated carbons are, unless otherwise specified, —R$^{60}$, halo, —O$^-$M$^+$, —OR$^{70}$, —SR$^{70}$, —S-M$^+$, —N(R$^{80}$)$_2$, perhaloalkyl, —CN, —OCN, —SCN, —NO, —NO$_2$, —N$_3$, —SO$_2$R$^{70}$, —SO$_3^-$M$^+$, —SO$_3$R$^{70}$, —OS$_2$R$^{70}$, —OSO$_3^-$M$^+$, —OSO$_3$R$^{70}$, —PO$_3^{-2}$(M$^+$)$_2$, —PO$_3^{-2}$M$^{2+}$, —P(O)(OR$^{70}$) O$^-$M$^+$, —P(O)(OR$^{70}$)$_2$, —C(O)R$^{70}$, —C(S)R$^{70}$, —C(NR$^{70}$) R$^{70}$, —CO$_2^-$M$^+$, —CO$_2$R$^{70}$, —C(S)OR$^{70}$, —C(O)NR$^{80}$R$^{80}$, —C(NR$^{70}$)N(R$^{80}$)$_2$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

Substituent groups for replacing hydrogen atoms on nitrogen atoms in groups containing such nitrogen atoms are, unless otherwise specified, —R$^{60}$, —O$^-$M$^+$, —OR$^{70}$, —SR$^{70}$, —S$^-$M$^+$, —N(R$^{80}$)$_2$, perhaloalkyl, —CN, —NO, —NO$_2$, —S(O)$_2$R$^{70}$, —SO$_3$$^-$M$^+$, —SO$_3$R$^{70}$, —OS(O)$_2$R$^{70}$, —OSO$_3$$^-$M$^+$, —OSO$_3$R$^{70}$, —PO$_3$$^{2-}$(M$^+$)$_2$, —PO$_3$$^2$, M$^{2+}$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined.

In one embodiment, a group that is substituted has 1 substituent, 2 substituents, substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, heterocyclic or aryl. Exemplary acyl moieties include, but are not limited to, —C(O)H, —C(O)alkyl, —C(O)C$_1$-C$_6$alkyl, —C(O)C$_1$-C$_6$haloalkyl-C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety, including alkyl, alkenyl, alkynyl groups, cyclic versions thereof, such as cycloalkyl, cycloalkenyl or cycloalkynyl, and further including straight- and branched-chain and bridged arrangements, and all stereo and position isomers as well. Unless expressly stated otherwise, an aliphatic group contains from one to twenty-five carbon atoms; for example, from one to fifteen, from one to ten, from one to six, or from one to four carbon atoms. "Lower aliphatic" refers to an aliphatic group containing from one to ten carbon atoms, such as from one to six, or from one to four carbon atoms. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, carboxamide, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, phosphate, or other functionality.

"Alkoxy" refers to the group —OR, where R is a substituted or unsubstituted alkyl group. In certain examples R is a C$_{1-6}$ alkyl group. Methoxy (—OCH$_3$) and ethoxy (—OCH$_2$CH$_3$) are exemplary alkoxy groups. In a substituted alkoxy, R is substituted alkyl, examples of which useful in the presently disclosed compounds include haloalkoxy groups, such as —OCF$_2$H.

"Alkoxyalkyl" refers to the group -alkyl-OR, where R is a substituted or unsubstituted alkyl group. —CH$_2$CH$_2$—O—CH$_2$CH$_3$ is an exemplary alkoxyalkyl group.

"Alkyl" refers to a saturated aliphatic hydrocarbyl group having from 1 to 25 carbon atoms, typically 1 to 10 carbon atoms such as 1 to 6 carbon atoms (C$_1$-C$_6$alkyl). An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$CH$_2$CH$_2$CH$_3$), isobutyl (—CH$_2$CH(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, heteroaliphatic, aryl or heterocyclic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^g$) such as in the groups

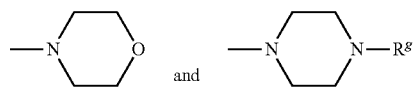

wherein R$^g$ is R$^{70}$, —C(O)R$^{70}$, —C(O)OR$^{60}$ or —C(O)N(R$^{80}$)$_2$.

"Amide" refers to the group —N(H)acyl, or —C(O)amino.

"Aryl" or "aromatic" refers to an aromatic group of, unless specified otherwise, from 5 to 15 ring atoms having a single ring (e.g., phenyl) or multiple fused rings in which at least one ring is aromatic (e.g., naphthyl). For groups having multiple rings, at least one of which is aromatic and one is not, such groups are nevertheless referred to as "aryl" provided that the point of attachment to the remainder of the compound is through an atom of an aromatic portion of the aryl group. Aryl groups may be monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxamide" refers to —C(O)NR$_2$, where the R groups may be the same or different, and generally are hydrogen, aliphatic, such as alkyl, and/or aryl. In particular embodiments, carboxamide refers to —C(O)NH$_2$.

"Carboxyl," "carboxy" or "carboxylate" refers to —CO₂H, —C(O)O— or salts thereof.

"Carboxyl ester" or "carboxy ester" refers to the group —C(O)OR, where R is aliphatic, heteroaliphatic, cyclic, and heterocyclic, including aryl and heteroaryl.

"Cyano" refers to the group —CN.

"Cycloaliphatic" refers to a cyclic aliphatic group having a single ring (e.g., cyclohexyl), or multiple rings, such as in a fused, bridged or spirocyclic system, at least one of which is aliphatic, provided that the point of attachment is through an atom of an aliphatic region of the cycloaliphatic group. Cycloaliphatic includes saturated and unsaturated systems, including cycloalkyl, cycloalkenyl and cycloalkynyl. A cycloaliphatic group may be unsubstituted or substituted, unless otherwise specified. Exemplary cycloaliphatic groups include, but are not limited to, cyclopropyl, cyclobutyl, cyclopentyl, cyclohexyl, cycloheptyl, cyclopentenyl, cyclohexenyl, or bicyclo[2.2.1]heptenyl.

"Halo," "halide" or "halogen" refers to fluoro, chloro, bromo or iodo.

"Haloalkyl" refers to an alkyl moiety substituted with one or more halogens. An exemplary haloalkyl moiety is $CF_3$.

"Heteroaliphatic" refers to an aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, acyclic or cyclic, such as a heteroalicyclyl group, chiral or achiral, and may include heterocycle, heterocyclyl, heterocycloaliphatic, or heterocyclic groups.

"Heteroaryl" refers to an aryl group where one or more carbon atoms, such as methine (—CH=) or vinylene (—CH=CH—) groups, have been replaced by trivalent or divalent heteroatoms, respectively, in such a way as to maintain aromaticity, such as determined by the continuous, delocalized π-electron system characteristic of the aromatic group, and the number of out of plane n-electrons corresponding to the Hückel rule (4n+2).

"Heterocycloalkyl" and "heterocyclylalkyl" refer to a heterocyclyl moiety attached to the parent structure via an alkyl moiety, for example, (tetrahydropyran-4-yl)methyl, (pyridine-4-yl)methyl, morpholinoethyl or piperazin-1-ylethyl.

"Heterocyclyl," "heterocyclo" and "heterocycle" refer to aromatic and non-aromatic ring systems, and more specifically refer to a stable three- to fifteen-membered ring moiety comprising carbon atoms and at least one, such as from one to five heteroatoms. Unless otherwise stated, a heterocyclyl group may be substituted or unsubstituted. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and the nitrogen, phosphorus, carbon, silicon or sulfur atoms in the heterocyclyl moiety can be optionally oxidized to various oxidation states. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is included as another compound of the invention, unless expressly excluded by context. In addition, annular nitrogen atoms can be optionally quaternized. Heterocycle includes heteroaryl moieties, and heteroalicyclyl or heterocycloaliphatic moieties, which are heterocyclyl rings which are partially or fully saturated. Thus a term such as "heterocyclylalkyl" includes heteroalicyclylalkyls and heteroarylalkyls. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO₂.

"Phosphate" refers to the group —O—P(O)(OR')₂, where each —OR' independently is —OH, —O-aliphatic, such as —O-alkyl, —O-aryl, or —O-aralkyl, or —OR' is —O⁻M⁺, where M⁺ is a counter ion with a single positive charge. Each M⁺ may be an alkali ion, such as K⁺, Na⁺, Li⁺; an ammonium ion, such as ⁺N(R")₄ where R" is H, aliphatic, heterocyclyl or aryl; or an alkaline earth ion, such as $[Ca^{2+}]_{0.5}$, $[Mg^{2+}]_{0.5}$, or $[Ba^{2+}]_{0.5}$. Alkyl phosphate refers to the group -alkyl-phosphate, such as, for example, —CH₂OP(O)(OH)₂, or a salt thereof, such as —CH₂OP(O)(O⁻Na⁺)₂.

"Phosphonate" refers to the group —P(O)(OR')₂, where each —OR' independently is —OH, —O-aliphatic such as —O-alkyl, —O-aryl, or —O-aralkyl, or where —OR' is —O⁻M⁺, and M⁺ is a counter ion with a single positive charge. Each M⁺ may be an alkali metal ion, such as K⁺, Na⁺, Li⁺; an ammonium ion, such as ⁺N(R")₄ where R" is H, aliphatic, heterocyclyl or aryl; or an alkaline earth metal ion, such as $[Ca^{2+}]_{0.5}$, $[Mg^{2+}]_{0.5}$, or $[Ba^{2+}]_{0.5}$. Alkyl phosphonate refers to the group -alkyl-phosphonate, such as, for example, —CH₂P(O)(OH)₂, or —CH₂P(O)(O⁻Na⁺)₂.

"Patient" or "Subject" refers to mammals and other animals, particularly humans. Thus disclosed methods are applicable to both human therapy and veterinary applications.

"Pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as freund's complete adjuvant or freund's incomplete adjuvant.

"Pharmaceutically acceptable carrier" refers to an excipient that is a carrier or vehicle, such as a suspension aid, solubilizing aid, or aerosolization aid. Pharmaceutically acceptable carriers are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the disclosed 2,4-diamino-pyrimidine compound may be a formate or sodium salt.

"Effective amount" refers to an amount of a compound or composition sufficient to achieve a particular desired result, such as to inhibit a protein or enzyme, particularly an IRAK or TAK enzyme; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the age of the patient to be treated, and the like.

"Prodrug" refers to compounds that are transformed in vivo to yield a biologically active compound, particularly the parent compound, for example, by hydrolysis in the gut or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press (1987), both of which are incorporated herein by reference for all purposes.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —N($R^c$)sulfonyl, where $R^c$ is H, aliphatic, heteroaliphatic, cyclic, and heterocyclic, including aryl and heteroaryl.

"Sulfanyl" refers to the group or —SH, —S-aliphatic, —S-heteroaliphatic, —S-cyclic, —S— heterocyclyl, including —S-aryl and —S-heteroaryl.

"Sulfinyl" refers to the group or moiety —S(O)H, —S(O)aliphatic, —S(O)heteroaliphatic, —S(O)cyclic, —S(O)heterocyclyl, including —S(O)aryl and —S(O)heteroaryl.

"Sulfonyl" refers to the group: —$SO_2$H, —$SO_2$aliphatic, —$SO_2$heteroaliphatic, —$SO_2$cyclic, —$SO_2$heterocyclyl, including —$SO_2$aryl and —$SO_2$heteroaryl.

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substitutents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the 2,4-diamino-pyrimidine and pryidyl rings, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium.

II. Background Information

IRAK4 kinase plays an important role in IL-1b/TLR signaling pathway, and is one of the key receptors that regulate innate immune response, which is associated with various inflammatory and cell proliferative disorders. From HTS screening and through hit-to-lead optimization, certain 2,4-diamino-pyrimidine compounds, including 5-aryl-2,4-diamino-pyrimidines, have been identified as potent IRAK4 inhibitors. IRAK4 co-crystal structure with an early lead molecule was obtained and was used to guide SAR analysis and new compound design. This series of compounds also exhibits high selectivity over TAK1 kinase, inhibition of which could cause liver toxicity and over-immunosuppression. Exemplary compounds according to the present invention have been evaluated in an acute IL-1b mouse model to demonstrate efficacy.

III. IRAK-Active Compounds and Compositions Comprising IRAK-Active Compounds

A. Compound Formulas

Compounds according to this disclosure may have a first Formula 1, below.

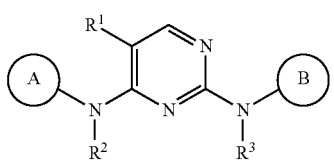

Formula 1

With reference to Formula 1, ring A is cycloaliphatic, such as (C6-C12) cycloalkyl, (C6-C12) cycloalkenyl, (C6-C12) bicycloalkyl, (C6-C12) bicycloalkenyl and substituted versions thereof, particularly carboxamide substituted versions, such as (—CONH$_2$)-substituted (C6-C12) cycloalkyl, cycloalkenyl, bicycloalkyl and bicycloalkenyl rings. In particular embodiments, ring A is a bridged bicyclic ring system. Ring B is selected from aryl, including unsubstituted aryl and substituted aryl, particularly phenyl and mono-, di- or tri-substituted phenyl. Exemplary aryl substituents are selected from (C1-10)amide, (C3-C10)cycloamide, (C1-C10)alkyl, particularly methyl, (C1-C10)alkoxyl, (C3-C10) cycloalkoxyl, halo (F, Cl, Br, I, and particularly F), (C3-C10)cycloalkyl, and (C3-C10)heterocycloalkyl. $R^1$ is selected from (C1-C10)alkyl, such as methyl; (C3-C10) cycloalkyl, such as cyclopropyl; halo (F, Cl, Br, I, and particularly F); aryl, such as phenyl, or substituted phenyl, such as halophenyl (e.g. fluorophenyl) and cyanophenyl; heteroaryl, such as pyridyl and furanyl; substituted heteroaryl, such as halopyridyl (e.g. fluoropyridyl). $R^2$ and $R^3$ are selected from hydrogen and (C1-C6)alkyl.

Compounds according to this disclosure may have a Formula 2, below.

Formula 2

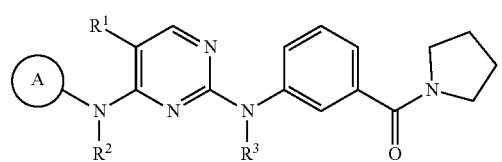

With reference to Formula 2, the A ring, and $R^1$, $R^2$ and $R^3$ are as stated above concerning Formula 1.

Compounds according to this disclosure may have a Formula 3, below.

Formula 3

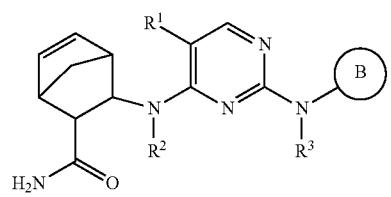

With reference to Formula 3, the B ring, and $R^1$, $R^2$ and $R^3$ are as stated above concerning Formula 1. Particular compounds according to Formula 3 had the following stereochemistry.

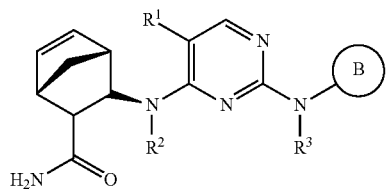

Particular examples of compounds according to Formula 1 had $R^1$ as aryl or heteroaryl, such as phenyl, e.g. Formula 4

Formula 4

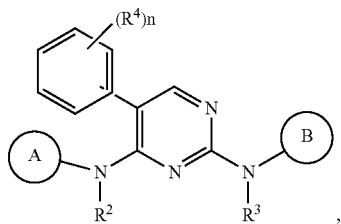

pyridyl, e.g. Formula 5

Formula 5

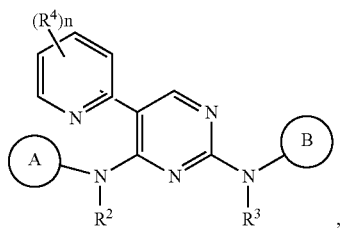

and furanyl, e.g. Formula 6

Formula 6

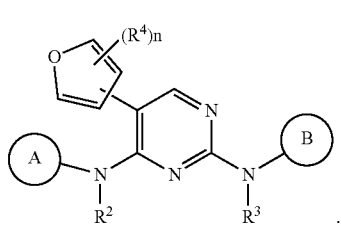

In other embodiments, the compound may have a formula selected from

Formula 7

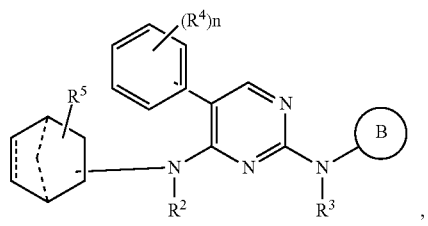

Formula 8

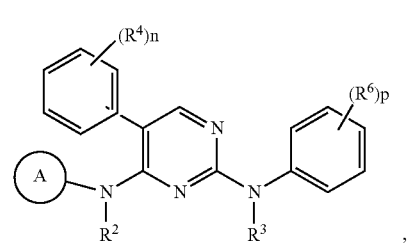

Formula 9

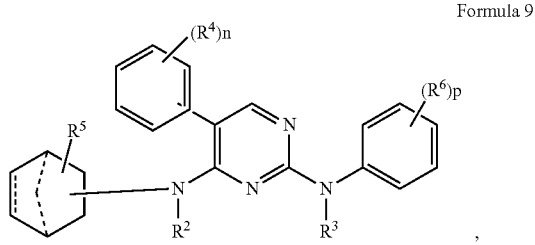

Formula 10

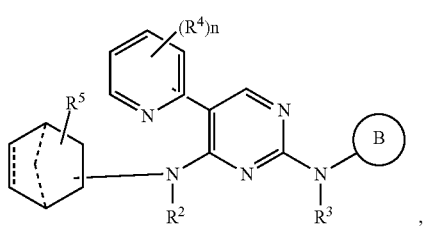

Formula 11

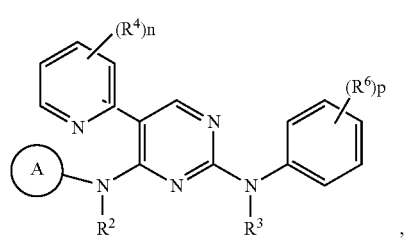

Formula 12

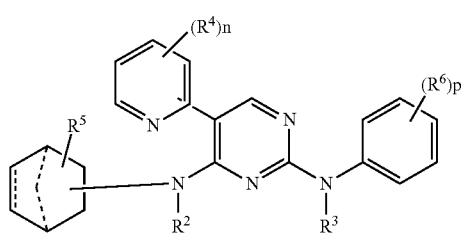

Formula 13

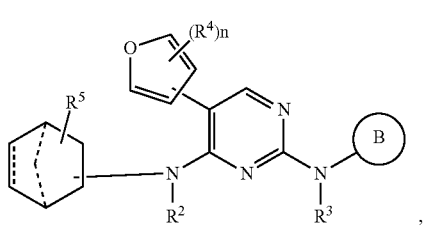

Formula 14

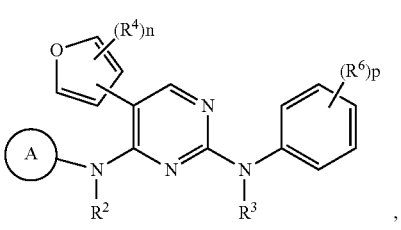

, or

Formula 15

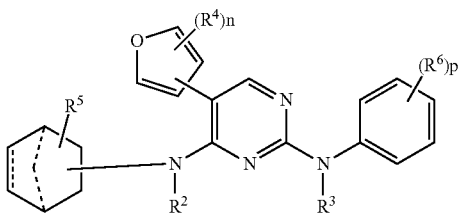

With reference to Formulas 4-15, $R^4$ is independently selected from (C1-C6)alkyl, such as methyl, cyano, and halo (F, Br, Cl and I, particularly F); n is equal to the number of possible substitution positions on a particular ring, generally 1, 2 or 3, and if n is 0, a person of ordinary skill in the art will understand that the compound includes the appropriate number of hydrogen atoms; $R^5$ may be CN or carboxamide, with particular compounds including (—C(O)NH$_2$); $R^6$ is selected from (C1-10)amide, (C3-C10)cycloamide, (C1-C10)alkyl, particularly methyl, (C1-C10)alkoxyl, (C3-C10) cycloalkoxyl, halo (F, Cl, Br, I, and particularly F), (C3-C10)cycloalkyl, or (C3-C10)heterocycloalkyl; p is 0, 1, 2, or 3, preferably 1 or 2; and a dashed line indicates an optional bond, e.g. ═ may be a single or double bond, and --- indicates that the bond may or may not be present.

$R^1$ also can be (C1-C10)alkyl (Formulas 16-19), such as methyl, or (C3-C10)cycloalkyl (Formulas 20-23), such as cyclopropyl.

Formula 16

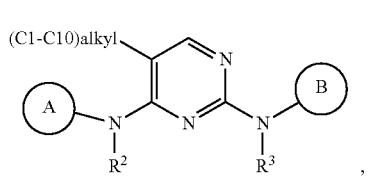

Formula 17

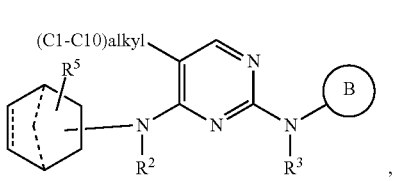

Formula 18

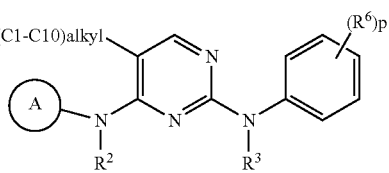

Formula 19

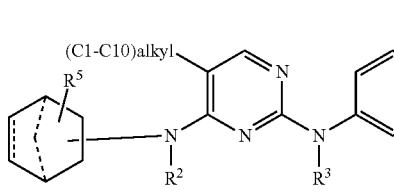

,

-continued

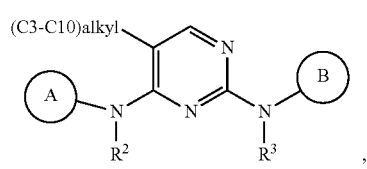
Formula 20

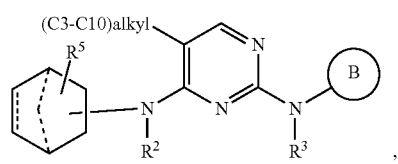
Formula 21

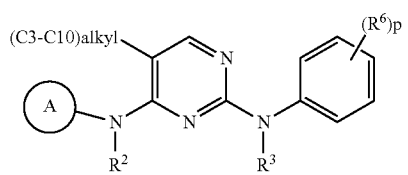
Formula 22

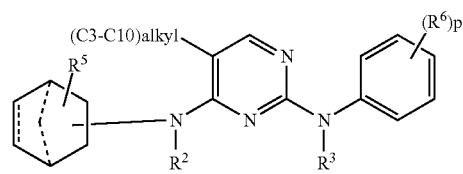
Formula 23

With respect to Formulas 16-23, ring A, ring B, $R^2$, $R^3$, $R^5$, $R^6$, and p are as defined above for Formulas 1-15.

In certain embodiments, the compound may have a formula selected from

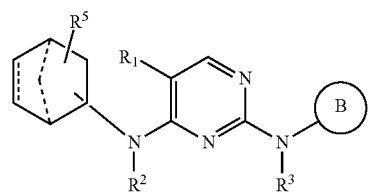
Formula 24

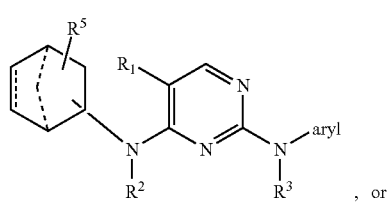
Formula 25, or

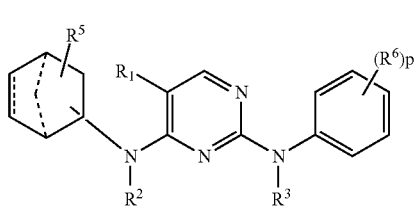
Formula 26

With respect to Formulas 24-26, ring B, $R^1$, $R^2$, $R^3$, $R^5$, $R^6$ and p are as defined above for Formulas 1-15.

In any of the above embodiments, particular A rings include

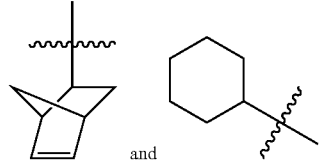

Particular carboxamide-substituted A rings include

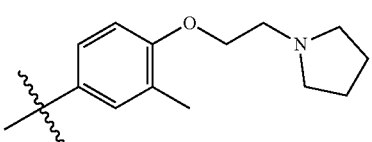

Particular exemplary compounds within the scope of the present invention include

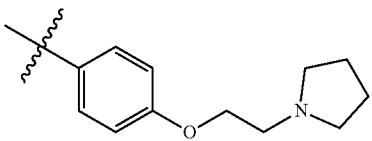

Particular B rings include

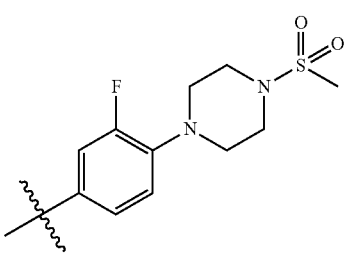

, and

-continued

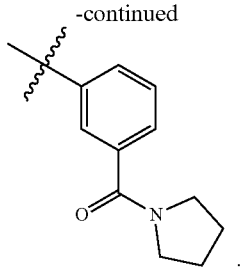

Particular R¹ substituents include CH₃,

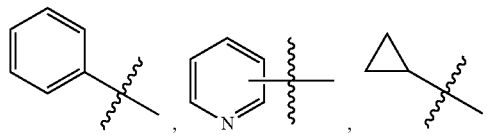

and substituted versions thereof, such as

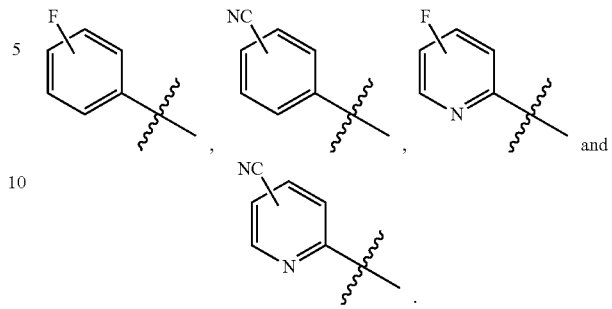

In any embodiments, R⁶ may be an amide, particularly

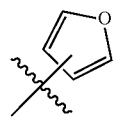

and p is 1. The amide may be at the 3-position of the phenyl ring.

Exemplary species satisfying one or more of Formulas 1-26 are provided below in Table 1. With reference to Table 1, table cells where no information is presented were not tested; A=<100 nM; B<250 nM; C<1 μM; and D>1 μM.

TABLE 1

| No. | COMPOUND STRUCTURE | COMPOUND NAME | IL23-p19 ELISA, THP1- IFNy, LPS, 10 pt | IL23-P19, ELISA, Dendritic, LPS, 10 pt |
|---|---|---|---|---|
| 1 | 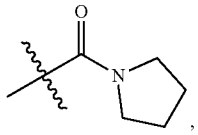 | 3-((2-((3-methyl-4-(2-(pyrrolidin-1-yl)ethoxy)phenyl)amino)-5-(pyridin-3-yl)pyrimidin-4-yl)amino)bicyclo[2.2.1]hept-5-ene-2-carboxamide | A | B |
| 2 | 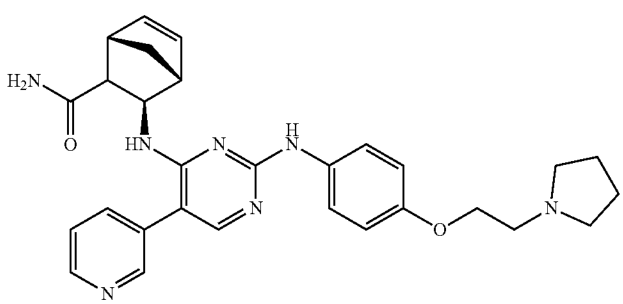 [SMILES: NC(=O)C1[C@@H]2C=C[C@@H](C2)[C@H]1Nc1nc(Nc2ccc(OCCN3CCCC3)cc2)ncc1-c1cccnc1] | 1S,2S,3R,4R)-3-((5-(pyridin-3-yl)-2-((4-(2-(pyrrolidin-1-yl)ethoxy)phenyl)amino)pyrimidin-4-yl)amino)bicyclo[2.2.1]hept-5-ene-2-carboxamide | | C |

TABLE 1-continued

| No. | COMPOUND STRUCTURE | COMPOUND NAME | IL23-p19 ELISA, THP1-IFNy, LPS, 10 pt | IL23-P19, ELISA, Dendritic, LPS, 10 pt |
|---|---|---|---|---|
| 3 | 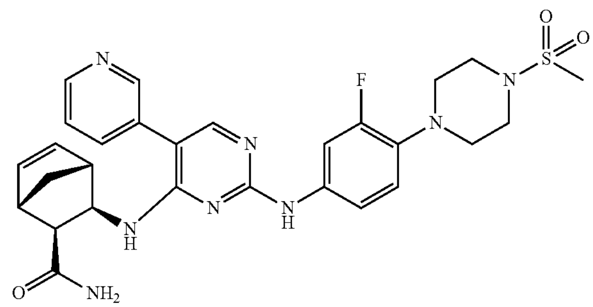 [SMILES: CS(=O)(=O)N1CCN(c2ccc(Nc3ncc(-c4cccnc4)c(N[C@H]4[C@@H](C(N)=O)[C@@H]5C=C[C@H]4C5)n3)cc2F)CC1] | (2S,3R)-3-((2-((3-fluoro-4-(4-(methyl sulfonyl) piperazin-1-yl)phenyl)amino)-5-(pyridin-3-yl)pyrimidin-4-yl)amino)bicyclo[2.2.1] hept-5-ene-2-carboxamide | C | |
| 4 | 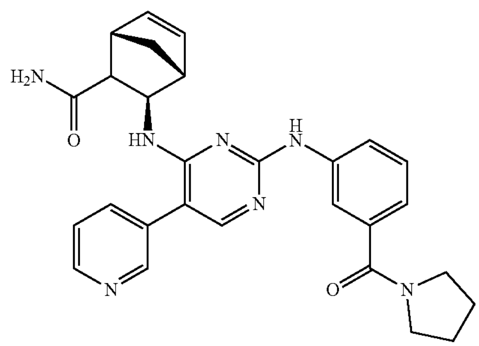 [SMILES: NC(=O)C1[C@@H]2C=C[C@@H](C2)[C@H]1Nc1nc(Nc2cccc(C(=O)N3CCCC3)c2)ncc1-c1cccnc1] | (1S,2S,3R,4R)-3-((5-(pyridin-3-yl)-2-((3-(pyrrolidine-1-carbonyl)phenyl)amino) pyrimidin-4-yl)amino)bicyclo[2.2.1] hept-5-ene-2-carboxamide | C | |
| 5 | 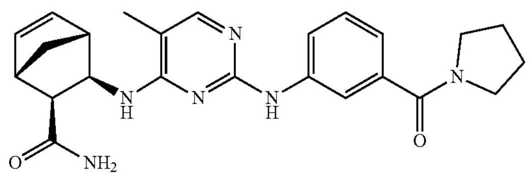 [SMILES: Cc1cnc(Nc2cccc(C(=O)N3CCCC3)c2)nc1N[C@H]1[C@@H](C(N)=O)[C@@H]2C=C[C@H]1C2] | (1S,2S,3R,4R)-3-((5-methyl-2-((3-(pyrrolidine-1-carbonyl)phenyl)amino) pyrimidin-4-yl)amino)bicyclo[2.2.1] hept-5-ene-2-carboxamide | A | |
| 6 | 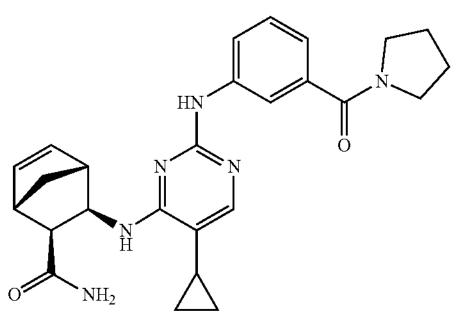 [SMILES: NC(=O)[C@@H]1[C@H](Nc2nc(Nc3cccc(C(=O)N4CCCC4)c3)ncc2C2CC2)[C@H]2C=C[C@@H]1C2] | (1S,2S,3R,4R)-3-((5-cyclopropyl-2-((3-(pyrrolidine-1-carbonyl)phenyl)amino) pyrimidin-4-yl)amino)bicyclo[2.2.1] hept-5-ene-2-carboxamide | A | A |
| 7 | 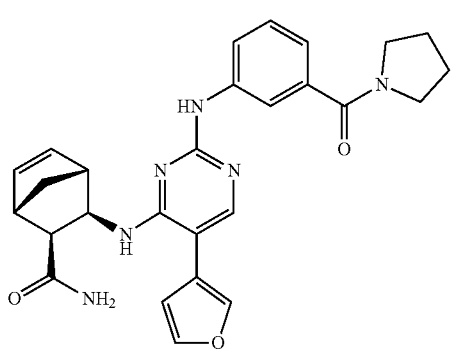 [SMILES: NC(=O)[C@@H]1[C@H](Nc2nc(Nc3cccc(C(=O)N4CCCC4)c3)ncc2-c2ccoc2)[C@H]2C=C[C@@H]1C2] | (1S,2S,3R,4R)-3-((5-(furan-3-yl)-2-((3-(pyrrolidine-1-carbonyl)phenyl)amino) pyrimidin-4-yl)amino)bicyclo[2.2.1] hept-5-ene-2-carboxamide | A | A |

TABLE 1-continued

| No. | COMPOUND STRUCTURE | COMPOUND NAME | IL23-p19 ELISA, THP1-IFNy, LPS, 10 pt | IL23-P19, ELISA, Dendritic, LPS, 10 pt |
|---|---|---|---|---|
| 8 | 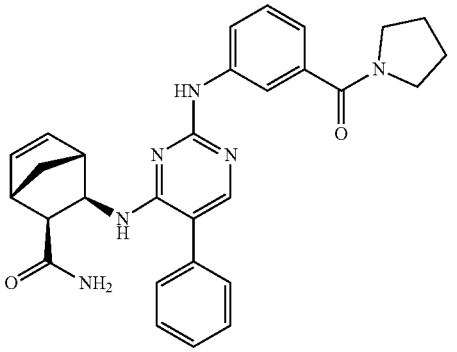 [SMILES: NC(=O)[C@@H]1[C@H](Nc2nc(Nc3cccc(C(=O)N4CCCC4)c3)ncc2-c2ccccc2)[C@H]2C=C[C@@H]1C2] | (1S,2S,3R,4R)-3-((5-phenyl-2-((3 (pyrrolidine-1-carbonyl)phenyl)amino) pyrimidin-4-yl)amino)bicyclo[2.2.1] hept-5-ene-2-carboxamide | B | C |
| 9 | 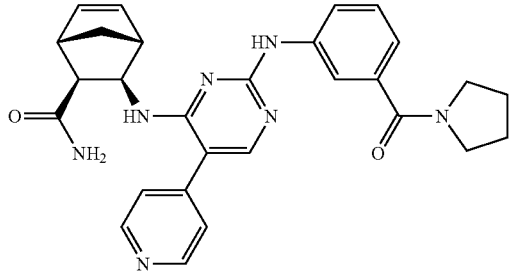 [SMILES: NC(=O)[C@@H]1[C@H](Nc2nc(Nc3cccc(C(=O)N4CCCC4)c3)ncc2-c2ccncc2)[C@H]2C=C[C@@H]1C2] | (1S,2S,3R,4R)-3-((5-(pyridin-4-yl)-2-((3-(pyrrolidine-1-carbonyl)phenyl)amino) pyrimidin-4-yl)amino)bicyclo[2.2.1] hept-5-ene-2-carboxamide | B | B |
| 10 | 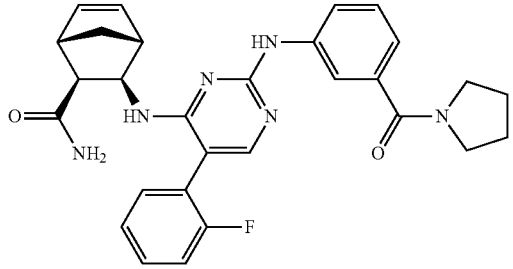 [SMILES: NC(=O)[C@@H]1[C@H](Nc2nc(Nc3cccc(C(=O)N4CCCC4)c3)ncc2-c2ccccc2F)[C@H]2C=C[C@@H]1C2] | (1S,2S,3R,4R)-3-((5-(2-fluorophenyl)-2-((3-(pyrrolidine-1-carbonyl)phenyl)amino) pyrimidin-4-yl)amino)bicyclo[2.2.1] hept-5-ene-2-carboxamide | C | |
| 11 | 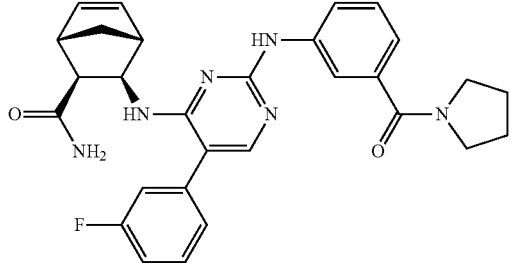 [SMILES: NC(=O)[C@@H]1[C@H](Nc2nc(Nc3cccc(C(=O)N4CCCC4)c3)ncc2-c2cccc(F)c2)[C@H]2C=C[C@@H]1C2] | (1S,2S,3R,4R)-3-((5-(3-fluorophenyl)-2-((3-(pyrrolidine-1-carbonyl)phenyl)amino) pyrimidin-4-yl)amino)bicyclo[2.2.1] hept-5-ene-2-carboxamide | B | A |
| 12 | 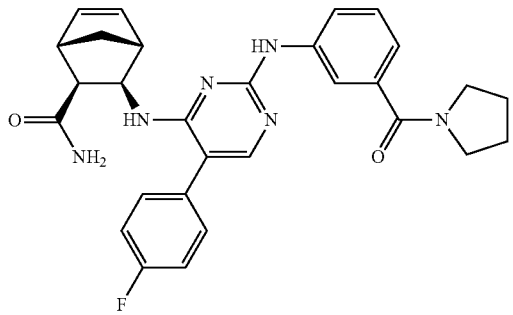 [SMILES: NC(=O)[C@@H]1[C@H](Nc2nc(Nc3cccc(C(=O)N4CCCC4)c3)ncc2-c2ccc(F)cc2)[C@H]2C=C[C@@H]1C2] | (1S,2S,3R,4R)-3-((5-(4-fluorophenyl)-2-((3 (pyrrolidine-1-carbonyl)phenyl)amino) pyrimidin-4-yl)amino)bicyclo[2.2.1] hept-5-ene-2-carboxamide | C | D |

TABLE 1-continued

| No. | COMPOUND STRUCTURE | COMPOUND NAME | IL23-p19 ELISA, THP1-IFNy, LPS, 10 pt | IL23-P19, ELISA, Dendritic, LPS, 10 pt |
|---|---|---|---|---|
| 13 | 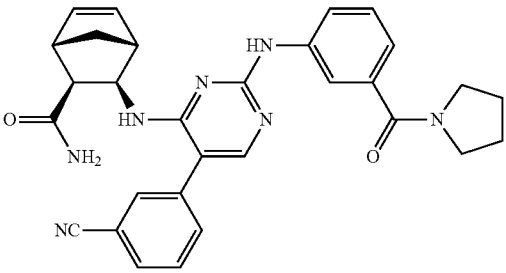 [SMILES: N#Cc1cccc(-c2cnc(Nc3cccc(C(=O)N4CCCC4)c3)nc2N[C@H]2[C@@H](C(N)=O)[C@@H]3C=C[C@H]2C3)c1] | (1S,2S,3R,4R)-3-((5-(3-cyanophenyl)-2-((3-(pyrrolidine-1-carbonyl)phenyl)amino)pyrimidin-4-yl)amino)bicyclo[2.2.1]hept-5-ene-2-carboxamide | C | C |
| 14 | 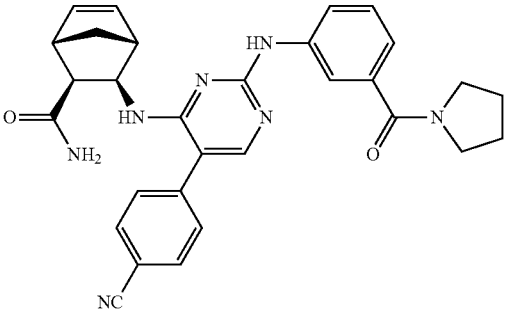 [SMILES: N#Cc1ccc(-c2cnc(Nc3cccc(C(=O)N4CCCC4)c3)nc2N[C@H]2[C@@H](C(N)=O)[C@@H]3C=C[C@H]2C3)cc1] | (1S,2S,3R,4R)-3-((5-(4-cyanophenyl)-2-((3-(pyrrolidine-1-carbonyl)phenyl)amino)pyrimidin-4-yl)amino)bicyclo[2.2.1]hept-5-ene-2-carboxamide | B | C |
| 15 | 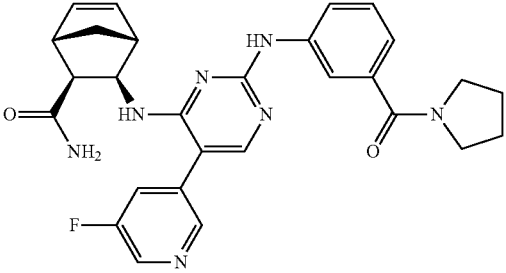 [SMILES: NC(=O)[C@@H]1[C@H](Nc2nc(Nc3cccc(C(=O)N4CCCC4)c3)ncc2-c2cncc(F)c2)[C@H]2C=C[C@@H]1C2] | (1S,2S,3R,4R)-3-((5-(5-fluoropyridin-3-yl)-2-((3-(pyrrolidine-1-carbonyl)phenyl)amino)pyrimidin-4-yl)amino)bicyclo[2.2.1]hept-5-ene-2-carboxamide | B | C |
| 16 | 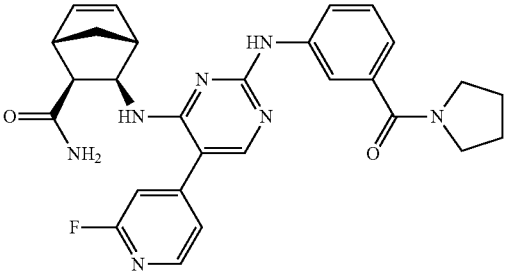 [SMILES: NC(=O)[C@@H]1[C@H](Nc2nc(Nc3cccc(C(=O)N4CCCC4)c3)ncc2-c2ccnc(F)c2)[C@H]2C=C[C@@H]1C2] | (1S,2S,3R,4R)-3-((5-(2-fluoropyridin-4-yl)-2-((3-(pyrrolidine-1-carbonyl)phenyl)amino)pyrimidin-4-yl)amino)bicyclo[2.2.1]hept-5-ene-2-carboxamide | A | B |
| 17 | 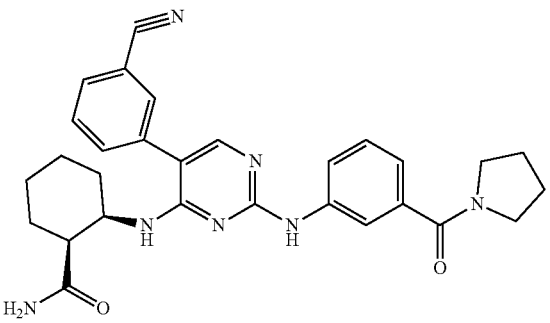 [SMILES: N#Cc1cccc(-c2cnc(Nc3cccc(C(=O)N4CCCC4)c3)nc2N[C@@H]2CCCC[C@@H]2C(N)=O)c1] | (1S,2R)-2-((5-(3-cyanophenyl)-2-((3-(pyrrolidine-1-carbonyl)phenyl)amino)pyrimidin-4-yl)amino)cyclohexane-1-carboxamide | C | |

TABLE 1-continued

| No. | COMPOUND STRUCTURE | COMPOUND NAME | IL23-p19 ELISA, THP1- IFNy, LPS, 10 pt | IL23-P19, ELISA, Dendritic, LPS, 10 pt |
|---|---|---|---|---|
| 18 | 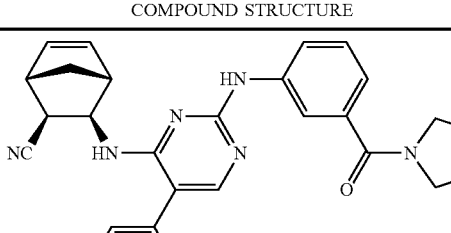 | (1S,2S,3R,4R)-3-((5-(3-cyanophenyl)-2-((3-(pyrrolidine-1-carbonyl)phenyl)amino)pyrimidin-4-yl)amino)bicyclo[2.2.1]hept-5-ene-2-carbonitrile | D | |

B. Compound Synthesis

Disclosed compounds can be prepared by any suitable method, with an exemplary method being illustrated below by Schemes 1 and 2, Examples 1-3, and as will be understood by a person of ordinary skill in the art of organic synthesis. Scheme 1 illustrates a general synthetic approach.

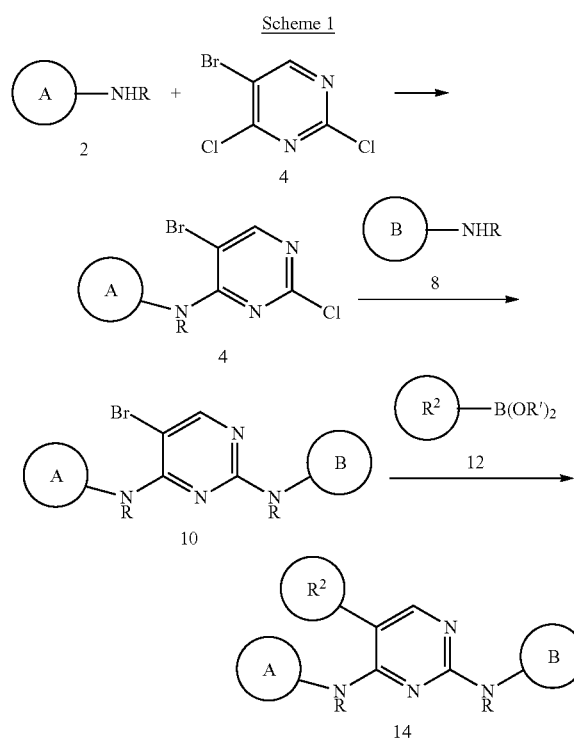

With reference to Scheme 1, primary or secondary amine 2 was reacted with 2,4-dichloro-5-bromo-pyrimidine 4 to form pyrimidineamine 6 having the appropriate regiochemistry by nucleophilic aromatic substitution. Pyrimidineamine 6 was then reacted with a primary or secondary amine 8 to form pyrimidinediamine 10, again having the appropriate regiochemistry, by nucleophilic aromatic substitution. Amines 2 and 8 are either primary or secondary amines. Accordingly, R is selected from hydrogen, aryl, aliphatic, cycloaliphatic, heteroaryl and cycloheteroaryl. R typically is either hydrogen or (C1-C10)alkyl, particularly methyl. Typical reaction conditions for formation of pyrimidineamine 6 are NaHCO$_3$ in slight excess, such as 1.1-1.5 equivalents, in a suitable solvent, such as an alkyl alcohol, generally at a temperature above room temperature. In particular embodiments, the reaction conditions were 1.3 equivalents of NaHCO$_3$ in isopropanol at 60° C. Typical conditions for formation of pyrimidinediamine 10 were trifluoroacetic acid (TFA) in excess, such as 2-3 equivalents TFA, in a suitable solvent, such as an alkyl alcohol, again generally at a temperature above room temperature. In certain embodiments, the reaction conditions were 2.5 equivalents of TFA in isopropanol at 90° C.

The 5-substituted pyrimidinediamine 14 was formed by a microwave reaction with an appropriate boronic acid and palladium reagent, in the presence of excess Na$_2$CO$_3$ and a suitable solvent. Formation of 5-substituted pyrimidinediamine 14 was accomplished in certain embodiments using 3 equivalents of 2M Na$_2$CO$_3$ in dioxane at 150° C. for 30 minutes.

Scheme 2 provides a more specific synthetic scheme with reference to particular compounds and stereochemistry for making certain exemplary compounds within the scope of the present invention.

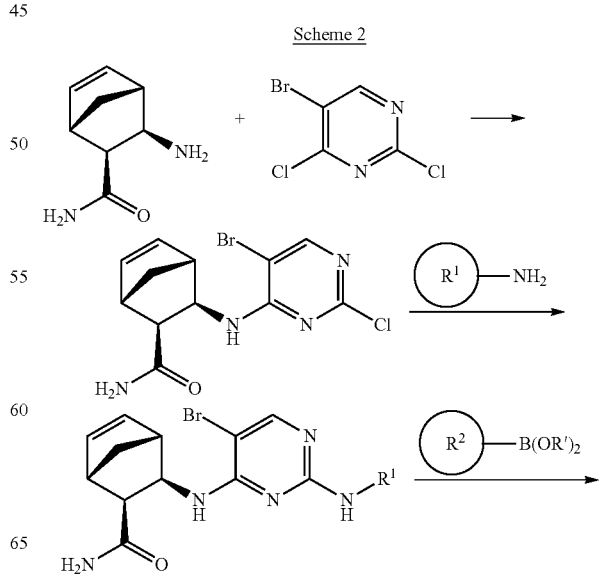

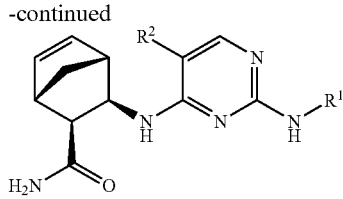

In a first particular embodiment with reference to Scheme 2 where $R^2$ is pyridinyl, a dimethyl ether-EtOH—$H_2O$ (7:3:2, 3 mL) solution of (1S,2S,3R,4R)-3-((5-bromo-2-((4-(2-(pyrrolidin-1-yl)ethoxy)phenyl)amino)pyrimidin-4-yl)amino)bicyclo[2.2.1]hept-5-ene-2-carboxamide (51.3 mg, 0.1 mmol), pyridin-3-ylboronic acid (18.4 mg, 0.15 mmol), Pd(PPh$_3$)$_4$ (11.6 mg, 0.01 mmol), and 2M aqueous solution of Na$_2$CO$_3$ (0.15 mL, 0.3 mmol) was microwaved at 150° C. for 30 minutes. Solid was removed by filtration and washed with MeOH. The filtrate was collected, solvent removed in vacuo, and product was purified by reverse-phase HPLC. The free base was obtained by passing a MeOH-product solution through a PL-HCO$_3$ column.

In a second particular embodiment where $R^2$ is cyclopropyl, a toluene/H$_2$O (2 mL/0.1 mL) suspension of (1S,2S,3R,4R)-3-((5-bromo-2-((3-(pyrrolidine-1-carbonyl)phenyl)amino)pyrimidin-4-yl)amino)bicyclo[2.2.1]hept-5-ene-2-carboxamide (0.08 mmol, 39.8 mg), cyclopropylboronic acid MIDA ester (0.12 mmol, 23.6 mg), Pd(OAc)$_2$ (0.008 mmol, 1.8 mg), tricyclohexylphosphine (0.016 mmol, 4.5 mg) and potassium phophosphate (0.24 mmol, 51 mg) was heated at 120° C. After 5 hours, the reaction was cooled to room temperature, and solid was removed by filtration. The product was purified by RP-HPLC. The TFA salt of the product was then free-based by passing a MeOH solution of the salt through a PL-HCO$_3$ column.

IV. Biological Data for Exemplary Compounds

IRAK4 kinase plays an important role in the IL-1b/TLR signaling pathway, and is one of the key receptors that regulate innate immune response, which is associated with various inflammatory and cell proliferative disorders. From HTS screening and through hit-to-lead optimization, compounds within the scope of the present disclosure, certain 2,4-diamino-pyrimidines, particularly 5-aryl-2,4-di amino-pyrimidines, have been identified as potent IRAK4 inhibitors. An IRAK4 co-crystal structure with an early lead molecule was obtained and was used to guide SAR analysis and the design of new compounds. This series of compounds also exhibit high selectivity for IRAK4 over TAK1 kinase, inhibition of which could cause liver toxicity and over-immunosuppression. TAK1 selectivity has been demonstrated using both different sizes and types of substituents at the 5-position of the pyrimidine ring. Certain representative compounds were evaluated in and acute IL-1b mouse model and demonstrated efficacy. IC$_{50}$ data for certain exemplary compounds is provided below in Table 2.

TABLE 2

| Compounds | R | IRAK4 | TAK1 | Selectivity (TAK1/IRAK4) | IL23 (LPS induced) |
|---|---|---|---|---|---|
| 5 | H$_3$C— | 0.003 | 0.008 | 3 | 0.10 |
| 6 | cyclopropyl | 0.006 | 0.011 | 2 | 0.09 |
| 7 | furan-3-yl | 0.002 | 0.011 | 5 | 0.04 |
| 8 | phenyl | 0.010 | 0.166 | 17 | 0.22 |
| 4 | pyridin-3-yl | 0.010 | 0.229 | 23 | 0.32 |

IC$_{50}$, μM

TABLE 2-continued

| Compounds | R | IC₅₀, μM | | | |
|---|---|---|---|---|---|
| | | IRAK4 | TAK1 | Selectivity (TAK1/IRAK4) | IL23 (LPS induced) |
| 9 | 4-pyridyl | 0.004 | 0.024 | 7 | 0.13 |
| 10 | 2-fluorophenyl | 0.011 | 4.8 | 434 | 0.87 |
| 11 | 3-fluorophenyl | 0.006 | 0.106 | 17 | 0.13 |
| 12 | 4-fluorophenyl | 0.019 | 0.670 | 35 | 0.46 |
| 13 | 3-cyanophenyl | 0.013 | 0.105 | 8 | 0.28 |
| 14 | 4-cyanophenyl | 0.009 | 1.6 | 170 | 0.19 |
| 15 | 5-fluoro-3-pyridyl | 0.005 | 0.056 | 12 | 0.17 |
| 16 | 2-fluoro-4-pyridyl | 0.003 | 0.017 | 5 | 0.10 |

Table 3 provides data illustrating the effects of substituents at the 4 position of the pyrimidine.

TABLE 3

| Compounds | R | IRAK4 | TAK1 | Selectivity (TAK1/IRAK4) | IL23 (LPS induced) |
|---|---|---|---|---|---|
| 17 | cyclohexyl-C(O)NH₂ | 0.030 | 0.067 | 2 | 0.9 |
| 18 | norbornenyl-CN | 3.7 | 132 | 36 | 3.4 |

Table 4 provides cell-based assay data for certain exemplary compounds according to the present invention.

TABLE 4

| | IC$_{50}$, µM | | IC$_{50}$, µM | | | Selectivity | | IC$_{50}$, µM | | | Selectivity | |
|---|---|---|---|---|---|---|---|---|---|---|---|---|
| Compounds | IL23 (THP, LPS) | IL23 (Dentritic Cells, LPS) | IL6 (HUVEC, LPS) | IL6 (HUVEC, IL-1β) | IL6 (HUVEC, TNFα) | IL6 (TNFα/ LPS) | IL6 (TNFα/ IL-1β) | IL8 (HUVEC, LPS) | IL8 (HUVEC, IL-1β) | IL8 (HUVEC, TNFα) | IL8 (TNFα/ LPS) | IL8 (TNFα/ IL-1β) |
| 11 | 0.13 | 0.07 | 0.13 | 0.14 | 1.7 | 13 | 12 | 0.95 | 0.31 | 6 | 6 | 18 |
| 15 | 0.17 | 0.51 | 0.18 | 0.20 | 0.9 | 5 | 5 | 1.10 | 0.29 | 14 | 13 | 48 |
| 16 | 0.10 | 0.11 | 0.12 | 0.11 | 1.2 | 9 | 11 | 1.00 | 0.25 | 3 | 3 | 12 |

These results establish that disclosed exemplary compounds within the scope of the present invention are potent IRAK4 and TAK1 inhibitors, and further that the compounds have substantial selectivity for IRAK4 relative to TAK1. For example, these results establish that the IC$_{50}$ for IRAK4 for exemplary compounds within the scope of the present invention was from 0.003 µM to 3.7 µM. The IC$_{50}$ for TAK1 was from 0.008 µM to 132 µM.

The selectivity of IRAK4 relative to TAK1 (IRAK4/TAK1) is also an important consideration. For certain exemplary compounds within the scope of the present invention the IRAK4/TAK1 selectivity was from 1 to 450, more generally 5 to 435. In certain embodiments, the IRAK4/TAK1 selectivity for 5-aryl substituted pyrimidinediamines was substantially higher than alkyl or cycloalkyl substituted compounds. For example, fluorophenyl-substituted pyrimidinediamines had an IRAK4/TAK1 selectivity greater than 400, with compound 10 having a selectivity of 434. Cyanophenyl-substituted pyrimidinediamines also had significant IRAK4/TAK1 selectivities over 150, with compound 14 having a selectivity of 170.

V. Combinations of Therapeutic Agents

The disclosed 2,4-diamino-pyrimidine compounds of the present invention may be used alone, in combination with one another, or as an adjunct to, or in combination with, other established therapies. In another aspect, the compounds of the present invention may be used in combination with other therapeutic agents useful for the disorder or condition being treated. These compounds may be administered simultaneously, sequentially in any order, by the same route of administration, or by a different route.

In some embodiments, the second therapeutic agent is an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a non-steroidal anti-inflammatory agent.

In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with other anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an antineoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhibitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608; marketed as EMPLICITI™), anti-KIR agents, such as the anti-KIR monoclonal antibody lirilumab (BMS-986015), and anti-CD137 agents, such as the fully human monoclonal antibody urelumab (BMS-663513).

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present disclosed 2,4-diamino-pyrimidine compounds include proteasome inhibitors, such as bortezomib, carfilzomib, marizomib and the like.

Examples of kinase inhibitors that are useful in combination with the presently disclosed compounds, particularly in treating malignancies include, Btk inhibitors, such as ibrutinib, CDK inhibitors, such as palbociclib, EGFR inhibitors, such as afatinib, erlotinib, gefitinib, lapatinib, osimertinib and vandetinib, Mek inhibitors, such as trametinib, Raf inhibitors, such as dabrafenib, sorafenib and vemurafenib, VEGFR inhibitors, such as axitinib, lenvatinib, nintedanib, pazopanib, BCR-Abl inhibitors, such as bosutinib, dasatinib, imatinib and nilotinib, Syk inhibitors, such as fostamatinib, and JAK inhibitors, such as ruxolitinib, In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, non-steroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues—for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

VI. Compositions Comprising Disclosed Compounds

The disclosed compounds may be used alone, in any combination, and in combination with, or adjunctive to, at least one second therapeutic agent, and further the disclosed 2,4-diamino-pyrimidine compounds, and the at least one second therapeutic, may be used in combination with any suitable additive useful for forming compositions for administration to a subject. Additives can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. Typical additives include, by way of example and without limitation: pharmaceutically acceptable excipients; pharmaceutically acceptable carriers; and/or adjuvants, such as mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene gylcols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

VII. Methods of Use

A. Diseases/Disorders

The disclosed 2,4-diamino-pyrimidine compounds, as well as combinations and/or compositions thereof, may be used to ameliorate, treat or prevent a variety of diseases and/or disorders. In particular embodiments, the disclosed 2,4-diamino-pyrimidine compound, combinations of the disclosed 2,4-diamino-pyrimidine compounds, or compositions thereof, may be used to treat or prevent auto-immune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, and bacterial and viral infections.

In some embodiments, the disclosed 2,4-diamino-pyrimidine compound, combinations of the disclosed 2,4-diamino-pyrimidine compounds, or compositions thereof, may be used to treat or prevent allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy or asthma.

The disclosed 2,4-diamino-pyrimidine compound, combinations of the disclosed 2,4-diamino-pyrimidine compounds, or compositions thereof, may also be useful for ameliorating, treating or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis *nodosa*, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the disclosed 2,4-diamino-pyrimidine compound, combinations of the disclosed 2,4-diamino-pyrimidine compounds, or compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, Parkinson's disease.

Proliferative diseases that may be treated by the disclosed 2,4-diamino-pyrimidine compound, combinations of the disclosed 2,4-diamino-pyrimidine compounds, or compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the disclosed 2,4-diamino-pyrimidine compound, combinations of the disclosed 2,4-diamino-pyrimidine compounds, or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed 2,4-diamino-pyrimidine compound, combinations of the disclosed 2,4-diamino-pyrimidine compounds, or compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration Pharmaceutical compositions comprising the active compounds of the invention (or prodrugs thereof) may be manufactured by means of conventional mixing, dissolving, granulating, dragee-making, levigating, emulsifying, encapsulating, entrapping or lyophilization processes. The compositions may be formulated in conventional manner using one or more physiologically acceptable excipients, diluents, carriers, adjuvants or auxiliaries to provide preparations which can be used pharmaceutically.

The active compound or prodrug may be formulated in the pharmaceutical compositions per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), hydrate, solvate, N-oxide or pharmaceutically acceptable salt or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, pharmaceutically acceptable salt or prodrug(s) can be conveniently delivered in the form of an aerosol spray from pressurized packs or a nebulizer with the use of a suitable propellant, e.g.,) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (1 4 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL Compound or prodrug, 1% (v/v) Polysorbate 80 (TWEEN® 80), 50 mM citrate and/or 0.9% sodium chloride.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active compound(s) or prodrug(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in, for example, U.S. Pat. Nos. 5,352,456; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s) or prodrug(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The disclosed 2,4-diamino-pyrimidine compound or combinations of the disclosed 2,4-diamino-pyrimidine compounds will generally be used in an amount effective to achieve the intended result, for example, in an amount effective to treat or prevent a particular condition. The disclosed 2,4-diamino-pyrimidine compound(s), or compositions thereof, can be administered therapeutically to achieve therapeutic benefit or prophylactically to achieve prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of disclosed 2,4-diamino-pyrimidine compounds will also depend on various factors, including the age, weight, general health, and severity of the condition of the patient or subject being treated. Dosage may also need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the disclosed 2,4-diamino-pyrimidine compound(s) or compositions thereof, will also depend on whether the disclosed 2,4-diamino-pyrimidine compound(s) are formulated for treatment of acute episodes of a condition or for the prophylactic treatment of a disorder. A person or ordinary skill in the art will be able to determine the optimal dose for a particular individual.

For prophylactic administration, the disclosed 2,4-diamino-pyrimidine compound, combinations of the disclosed 2,4-diamino-pyrimidine compounds, or compositions thereof, can be administered to a patient or subject at risk of developing one of the previously described conditions. For example, if it is unknown whether a patient or subject is allergic to a particular drug, the disclosed 2,4-diamino-pyrimidine compound, combinations of the disclosed 2,4-diamino-pyrimidine compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a disclosed 2,4-diamino-pyrimidine compound(s), or composition thereof, can be administered to an allergy sufferer prior to expected exposure to the allergen. A disclosed 2,4-diamino-pyrimidine compound, combinations of the disclosed 2,4-diamino-pyrimidine compounds, or compositions thereof, can also be administered prophylactically to healthy individuals who are repeatedly exposed to agents known to one of the above-described maladies to prevent the onset of the disorder. For example, a disclosed 2,4-diamino-pyrimidine compound, combinations of the disclosed 2,4-diamino-pyrimidine compounds, or compositions thereof, can be administered to a healthy individual who is repeatedly exposed to an allergen known to induce allergies, such as latex, in an effort to prevent the individual from developing an allergy. Alternatively, a disclosed 2,4-diamino-pyrimidine compound, combinations of the disclosed 2,4-diamino-pyrimidine compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, or from greater than 0 to 0.1 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11): 1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed 2,4-diamino-pyrimidine compounds will typically be in the range of from about greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the disclosed 2,4-diamino-pyrimidine compound, its bioavailability, the mode of administration, and various factors discussed above.

Dosage amount and dosage interval can be adjusted for individuals to provide plasma levels of the disclosed 2,4-diamino-pyrimidine compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed 2,4-diamino-pyrimidine compounds typically comprise from greater than 0 up to 99% of the disclosed 2,4-diamino-pyrimidine compound, or compounds, and/or other therapeutic agent by total weight percent. More typically, compositions comprising one or more of the disclosed 2,4-diamino-pyrimidine compounds comprise from about 1 to about 20 total weight percent of the disclosed 2,4-diamino-pyrimidine compound and other therapeutic agent, and from about 80 to about 99 weight percent of a pharmaceutically acceptable additive.

Preferably, the disclosed 2,4-diamino-pyrimidine compound, combinations of the disclosed 2,4-diamino-pyrimidine compounds, or compositions thereof, will provide therapeutic or prophylactic benefit without causing substantial toxicity. Toxicity of the disclosed 2,4-diamino-pyrimidine compound can be determined using standard pharmaceutical procedures. The dose ratio between toxic and therapeutic (or prophylactic) effect is the therapeutic index. disclosed 2,4-diamino-pyrimidine compounds that exhibit high therapeutic indices are preferred.

VIII. Biological Assays

IRAK4 and TAK1 biochemical assays: kinase activity was measured by ADP-Glo kinase assay (Promega).

IL-23 assays: THP1 cells or human primary monocyte-derived dendritic cells (DC) were primed overnight with IFNg. Following one hour preincubation with compound, cells were stimulated overnight with LPS. IL-23 released into the media was quantitated by ELISA.

IL-6 and IL-8 assays: Human umbilical vein endothelial cells (Huvec) were preincubated with compound for 1 hour, then stimulated overnight with either IL1b or TNFa. IL-6 and IL-8 release into the media and quantitated by ELISA.

A series of disclosed 2,4-diamino-pyrimidine compounds have been developed as potent IRAK4 inhibitors, with good selectivity over TAK1 kinase. Co-crystal structures of compound 11 with both IRAK4 and TAK1, and gained valuable knowledge for designing selective IRAK4 inhibitors. Moieties have been identified that are responsible for on-target potency and key factors that lead to high selectivity.

IX. EXAMPLES

Example 1

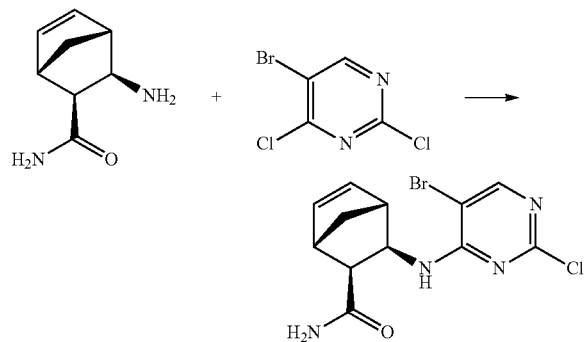

The conditions for this reaction were NaHCO$_3$ (1.3 equivalents), in isopropyl alcohol, at 60° C.

Example 2

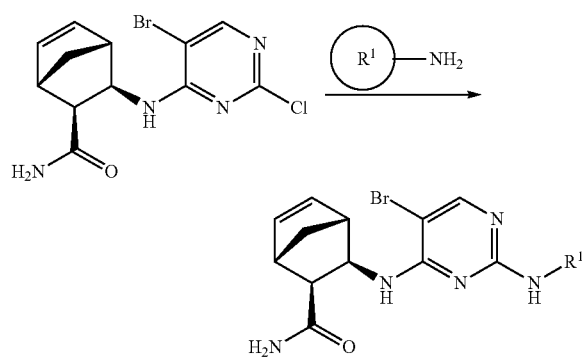

The conditions for this reaction were trifluoroacetic acid (2.5 equivalents) in isopropyl alcohol, at a temperature of 90° C.

Example 3

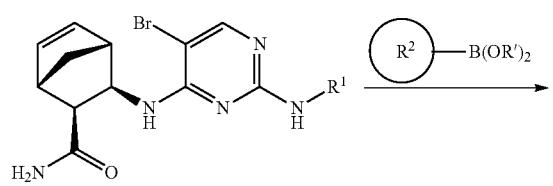

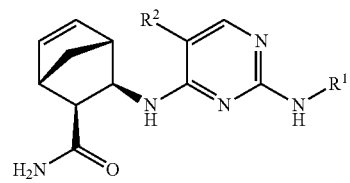

The conditions for this reaction were R—B(OR)$_2$, Pd(PPH$_3$)$_4$, Na$_2$CO$_3$ (2M aqueous, 3 equivalents), in dioxane, microwave, at 150° C., 30 minutes.

Example 4

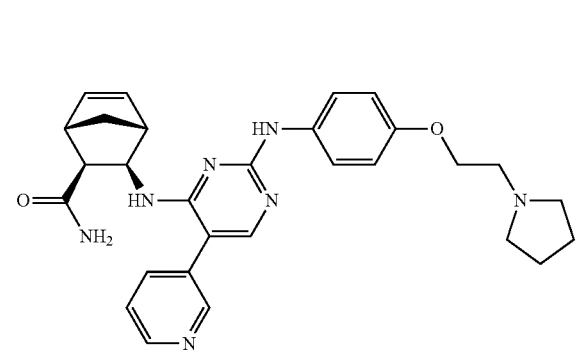 [SMILES: NC(=O)[C@@H]1[C@H](Nc2nc(Nc3ccc(OCCN4CCCC4)cc3)ncc2-c2cccnc2)[C@H]2C=C[C@@H]1C2]

(1S,2S,3R,4R)-3-((5-(pyridin-3-yl)-2-((4-(2-(pyrrolidin-1-yl)ethoxy)phenyl)amino)pyrimidin-4-yl)amino)bicyclo[2.2.1]hept-5-ene-2-carboxamide A DME-EtOH—H$_2$O (7:3:2, 3 mL) solution of (1S,2S,3R,4R)-3-((5-bromo-2-((4-(2-(pyrrolidin-1-yl)ethoxy)phenyl)amino)pyrimidin-4-yl)amino)bicyclo[2.2.1]hept-5-ene-2-carboxamide (51.3 mg, 0.1 mmol), pyridin-3-ylboronic acid (18.4 mg, 0.15 mmol), Pd(PPh$_3$)$_4$ (11.6 mg, 0.01 mmol), and 2M aqueous solution of Na$_2$CO$_3$ (0.15 mL, 0.3 mmol) was microwaved at 150° C. for 30 minutes. Solid was removed by filtration through a short celite pad, and washed with MeOH. The filtrate was collected, solvent removed in vacuo, and product was purified by reverse-phase HPLC, then subsequent free-basing by passing a MeOH-product solution through a PL-HCO$_3$ column, washing with MeOH. Filtrate was collected, solvent was removed in vacuo. Compound (1S,2S,3R,4R)-3-((5-(pyridin-3-yl)-2-((4-(2-(pyrrolidin-1-yl)ethoxy)phenyl)amino)pyrimidin-4-yl)amino)bicyclo[2.2.1]hept-5-ene-2-carboxamide was obtained as a white solid: 19.5 mg (38% yield): 1H NMR (300 MHz, DMSO-d6) δ 9.11 (s, 1H), 8.59 (d, J=2.3 Hz, 1H), 8.57 (dd, J=4.8, 1.6 Hz, 1H), 7.85 (s, 1H), 7.81 (ddd, J=7.9, 2.0, 2.0 Hz, 1H), 7.73-7.69 (m, 3H), 7.48 (dd, J=7.9, 5.5 Hz, 1H), 7.42 (d, J=7.2 Hz, 1H), 7.20 (s, 1H), 6.91-6.87 (m, 2H), 6.38-6.34 (m, 2H), 4.21 (dd, J=7.9, 7.9 Hz, 1H), 4.07 (t, J=6.0 Hz, 2H), 2.89 (s, 1H), 2.88 (s, 1H), 2.80 (t, J=6.0 Hz, 2H), 2.58-2.53 (m, overlapped with DMSO, 4H), 2.48 (d, J=8.3 Hz, 1H), 2.00 (d, J=8.5 Hz, 1H), 1.77-1.68 (m, 4H), 1.41 (d, J=8.4 Hz, 1H); LRMS (M+H) m/z 512.44.

Example 5

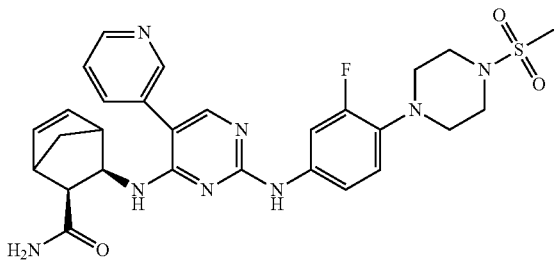 [SMILES: CS(=O)(=O)N1CCN(c2ccc(Nc3ncc(-c4cccnc4)c(N[C@@H]4C5C=CC(C5)[C@@H]4C(N)=O)n3)cc2F)CC1]

(2S,3R)-3-((2-((3-fluoro-4-(4-(methylsulfonyl)piperazin-1-yl)phenyl)amino)-5-(pyridin-3-yl)pyrimidin-4-yl)amino)bicyclo[2.2.1]hept-5-ene-2-carboxamide

Example 6

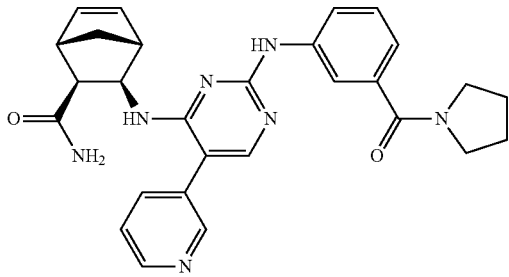 [SMILES: NC(=O)[C@@H]1[C@H](Nc2nc(Nc3cccc(C(=O)N4CCCC4)c3)ncc2-c2cccnc2)[C@H]2C=C[C@@H]1C2]

(1S,2S,3R,4R)-3-((5-(pyridin-3-yl)-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H$_2$O (7:3:2, 3 mL) as solvent, with pyridin-3-ylboronic acid, 22 mg, 44% yield.

$^1$H NMR (300 MHz, DMSO-d6) δ 9.46 (s, 1H), 8.61 (br d, J=2.3 Hz, 1H), 8.59 (br d, J=4.8 Hz, 1H), 8.08 (br s, 1H), 7.91 (s, 1H), 7.86-7.82 (m, 2H), 7.73 (br s, 1H), 7.54 (d, J=6.9 Hz, 1H), 7.50 (dd, J=7.9, 3.2 Hz, 1H), 7.35 (dd, J=7.9 Hz, 1H), 7.21 (br s, 1H), 7.04 (d, J=7.6 Hz, 1H), 6.35 (dd, J=5.8, 2.8 Hz, 1H), 6.27 (dd, J=5.8, 2.8 Hz, 1H), 4.21 (dd, J=7.7, 7.7 Hz, 1H), 3.49 (dd, J=6.7, 6.7 Hz, 2H), 3.41 (dd, J=6.7, 6.7 Hz, 2H), 2.87 (s, 1H), 2.83 (s, 1H), 2.48 (d, J=8.1 Hz, 1H), 2.00 (d, J=8.7 Hz, 1H), 1.93-1.82 (m, 4H), 1.40 (d, J=8.4 Hz, 1H); LRMS (M+H) m/z 496.42.

Example 7

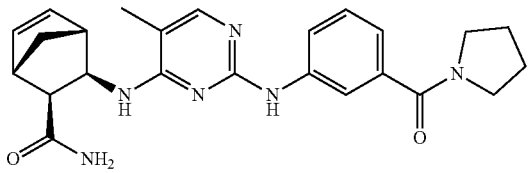 [SMILES: Cc1cnc(Nc2cccc(C(=O)N3CCCC3)c2)nc1N[C@H]1[C@@H](C(N)=O)[C@@H]2C=C[C@H]1C2]

(1S,2S,3R,4R)-3-((5-methyl-2-((3-(pyrrolidine-1-carbonyl)phenyl)amino)pyrimidin-4-yl)amino)bicyclo[2.2.1]hept-5-ene-2-carboxamide 0.1 mmol scale, with (3-aminophenyl)(pyrrolidin-1-yl)methanone, 26.6 mg, 61% yield.

$^1$H NMR (300 MHz, DMSO-d6) δ 9.11 (s, 1H), 8.07-8.05 (m, 1H), 7.81-7.74 (m, 3H), 7.33-7.26 (m, 2H), 7.20 (d, J=7.7 Hz, 1H), 6.97 (dd, J=7.5, 1.2 Hz, 1H), 6.36 (dd, J=5.7, 2.8 Hz, 1H), 6.28 (dd, J=5.7, 2.8 Hz, 1H), 4.16 (dd, J=9.0, 6.9 Hz, 1H), 3.51-3.46 (m, partially overlapped with H2O, 4H), 2.89 (s, 1H), 2.80 (s, 1H), 2.58-2.53 (m, 4H, overlapped with DMSO), 2.16 (d, J=8.6 Hz, 1H), 1.90 (s, 3H), 1.90-1.82 (m, 4H), 1.43 (d, J=8.6 Hz, 1H); LRMS (M+H) m/z 433.36.

Example 8

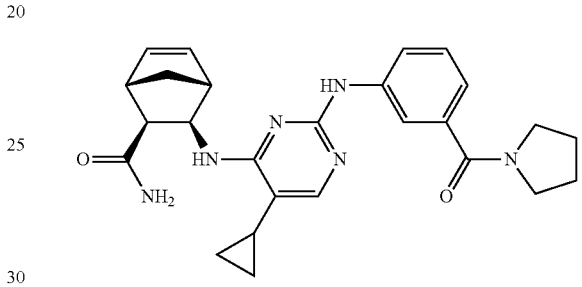

(1S,2S,3R,4R)-3-((5-cyclopropyl-2-((3-(pyrrolidine-1-carbonyl)phenyl)amino)pyrimidin-4-yl)amino)bicyclo[2.2.1]hept-5-ene-2-carboxamide A toluene/H$_2$O (2 mL/0.1 mL) suspension of (1S,2S,3R,4R)-3-((5-bromo-2-((3-(pyrrolidine-1-carbonyl)phenyl)amino)pyrimidin-4-yl)amino)bicyclo[2.2.1]hept-5-ene-2-carboxamid (0.08 mmol, 39.8 mg), cyclopropylboronic acid MIDA ester (0.12 mmol, 23.6 mg), Pd(OAc)$_2$ (0.008 mmol, 1.8 mg), tricyclohexylphosphine (0.016 mmol, 4.5 mg) and potassium phophosphate (0.24 mmol, 51 mg) was heated at 120° C. After 5 hours, the reaction was cooled to room temperature, solid was removed by filtration through a celite pad, and washed with MeOH. Filtrate was collected and solvent was removed in vacuo. Product was purified by RP-HPLC, TFA salt of the product was then free-based by passing a MeOH solution of the salt through a PL-HCO3 column, washing with MeOH. Filtrate was collected and solvent was removed in vacuo. Compound (1S,2S,3R,4R)-3-((5-cyclopropyl-2-((3-(pyrrolidine-1-carbonyl)phenyl)amino)pyrimidin-4-yl)amino)bicyclo[2.2.1]hept-5-ene-2-carboxamide was obtained as a light yellow solid: 4.5 mg (12% yield):

$^1$H NMR (300 MHz, DMSO-d6) δ 9.16 (s, 1H), 8.08 (br s, 1H), 7.80-7.77 (m, 2H), 7.71 (br s, 1H), 7.51 (d, J=7.8 Hz, 1H), 7.30 (t, J=7.9 Hz, 1H), 7.23 (br s, 1H), 6.97 (d, J=7.6 Hz, 1H), 6.37 (dd, J=5.9, 2.9 Hz, 1H), 6.28 (dd, J=5.6, 2.9 Hz, 1H), 4.18 (dd, J=8.2, 8.2 Hz, 1H), 3.41-3.46 (m, partially overlapped with H2O, 4H), 2.90 (s, 1H), 2.80 (s, 1H), 2.58-2.53 (m, 4H, overlapped with DMSO), 2.20 (d, J=8.6 Hz, 1H), 1.92-1.79 (m, 4H), 1.44 (d, J=8.6 Hz, 1H), 1.40-1.31 (m, 1H), 0.86-0.83 (m, 2H), 0.53-0.43 (m, 2H); LRMS (M+H) m/z 459.53.

Example 9

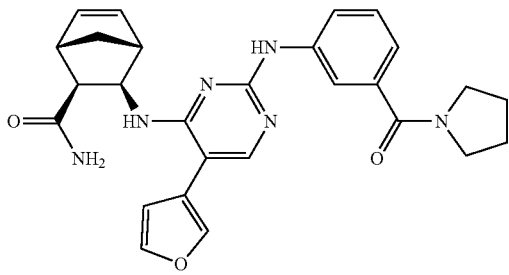 [SMILES: NC(=O)[C@@H]1[C@H](Nc2nc(Nc3cccc(C(=O)N4CCCC4)c3)ncc2-c2ccoc2)[C@H]2C=C[C@@H]1C2]

(1S,2S,3R,4R)-3-((5-(furan-3-yl)-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H2O (7:3:2, 3 mL) as solvent, with furan-3-ylboronic acid, 21.7 mg, 45% yield.

$^1$H NMR (300 MHz, DMSO-d6) δ 9.39 (s, 1H), 8.07 (s, 1H), 8.05 (br s, 1H), 7.91 (br s, 1H), 7.85-7.81 (m, 3H), 7.37-7.31 (m, 2H), 7.20 (d, J=7.9 Hz, 1H), 7.03 (d, J=7.5 Hz, 1H), 6.82 (br s, 1H), 6.36 (dd, J=5.8, 2.9 Hz, 1H), 6.28 (dd, J=5.8, 2.9 Hz, 1H), 4.30 (br dd, J=9.0, 9.0 Hz, 1H), 3.49 (dd, J=6.7, 6.7 Hz, 2H), 3.40 (dd, J=6.7, 6.7 Hz, 2H), 2.87 (s, 1H), 2.80 (s, 1H), 2.55-2.53 (1H, overlapped with DMSO), 2.11 (d, J=8.9 Hz, 1H), 1.98-1.76 (m, 4H), 1.43 (d, J=8.9 Hz, 1H); LRMS (M+H) m/z 485.49.

Example 10

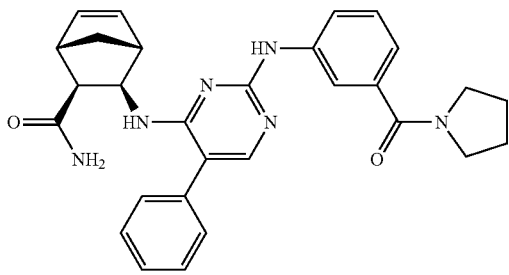 [SMILES: NC(=O)[C@@H]1[C@H](Nc2nc(Nc3cccc(C(=O)N4CCCC4)c3)ncc2-c2ccccc2)[C@H]2C=C[C@@H]1C2]

(1S,2S,3R,4R)-3-((5-phenyl-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H2O (7:3:2, 3 mL) as solvent, with phenylboronic acid, 12.7 mg, 26% yield.

$^1$H NMR (300 MHz, DMSO-d6) δ 9.38 (s, 1H), 8.07 (br s, 1H), 7.87-7.84 (m, 2H), 7.50 (s, 1H), 7.51-7.30 (m, 7H), 7.17 (s, 1H), 7.03 (d, J=7.7 Nz, 1H), 6.34 (dd, J=5.7, 2.8 Hz, 1H), 6.28 (dd, J=5.7, 2.8 Hz, 1H), 4.25 (dd, J=8.0, 8.0 Hz, 1H), 3.49 (dd, J=6.7, 6.7 Hz, 2H), 3.41 (dd, J=6.7, 6.7 Hz, 2H), 2.82 (br s, 2H), 2.48 (d, J=8.2 Hz, 1H), 2.01 (d, J=8.2 Hz, 1H), 1.93-1.82 (m, 4H), 1.40 (d, J=8.7 Hz, 1H); LRMS (M+H) m/z 495.51.

Example 11

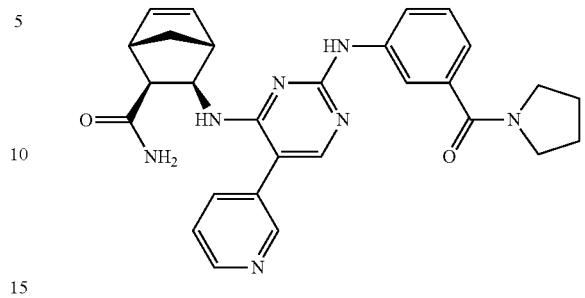

(1S,2S,3R,4R)-3-((5-(pyridin-3-yl)-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H2O (7:3:2, 3 mL) as solvent, with pyridin-3-ylboronic acid, 22 mg, 44% yield.

$^1$H NMR (300 MHz, DMSO-d6) δ 9.46 (s, 1H), 8.61 (br d, J=2.3 Hz, 1H), 8.59 (br d, J=4.8 Hz, 1H), 8.08 (br s, 1H), 7.91 (s, 1H), 7.86-7.82 (m, 2H), 7.73 (br s, 1H), 7.54 (d, J=6.9 Hz, 1H), 7.50 (dd, J=7.9, 3.2 Hz, 1H), 7.35 (dd, J=7.9 Hz, 1H), 7.21 (br s, 1H), 7.04 (d, J=7.6 Hz, 1H), 6.35 (dd, J=5.8, 2.8 Hz, 1H), 6.27 (dd, J=5.8, 2.8 Hz, 1H), 4.21 (dd, J=7.7, 7.7 Hz, 1H), 3.49 (dd, J=6.7, 6.7 Hz, 2H), 3.41 (dd, J=6.7, 6.7 Hz, 2H), 2.87 (s, 1H), 2.83 (s, 1H), 2.48 (d, J=8.1 Hz, 1H), 2.00 (d, J=8.7 Hz, 1H), 1.93-1.82 (m, 4H), 1.40 (d, J=8.4 Hz, 1H); LRMS (M+H) m/z 496.42.

Example 12

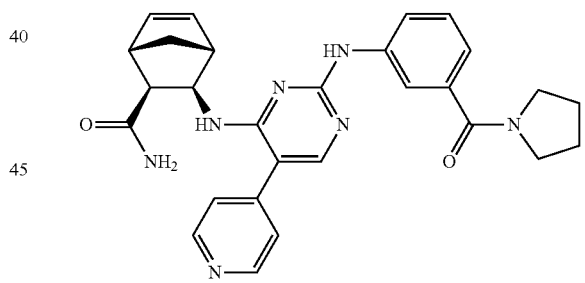

(1S,2S,3R,4R)-3-((5-(pyridin-4-yl)-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H2O (7:3:2, 3 mL) as solvent, with pyridin-4-ylboronic acid, 24.8 mg, 39% yield.

$^1$H NMR (300 MHz, DMSO-d6) δ 9.54 (s, 1H), 8.65-8.62 (m, 2H), 8.07 (s, 1H), 8.00 (s, 1H), 7.85 (d, J=8.3 Hz, 1H), 7.78 (s, 1H), 7.64 (d, J=7.2 Hz, 1H), 7.46-7.44 (m, 2H), 7.36 (dd, J=7.9, 7.9 Hz, 1H), 7.27 (s, 1H), 7.06 (d, J=7.5 Hz, 1H), 6.36 (dd, J=5.7, 2.8 Hz, 1H), 6.27 (dd, J=5.7, 2.8 Hz, 1H), 4.23 (dd, J=7.5, 7.5 Hz, 1H), 3.49 (dd, J=6.5, 6.5 Hz, 2H), 3.41 (dd, J=6.5, 6.5 Hz, 2H), 2.86 (br s, 2H), 2.50 (d, J=8.2 Hz, 1H), 2.04 (d, J=8.8 Hz, 1H), 1.92-1.83 (m, 4H), 1.42 (d, J=8.8 Hz, 1H); LRMS (M+H) m/z 496.49.

Example 13

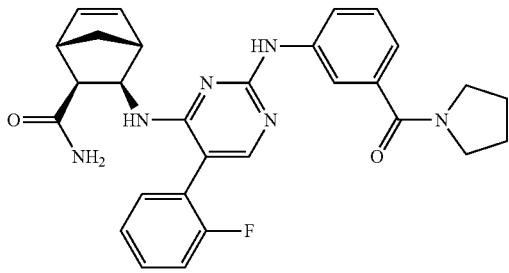 [SMILES: NC(=O)[C@@H]1[C@H](Nc2nc(Nc3cccc(C(=O)N4CCCC4)c3)ncc2-c2ccccc2F)[C@H]2C=C[C@@H]1C2]

(1S,2S,3R,4R)-3-((5-(2-fluorophenyl)-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H2O (7:3:2, 3 mL) as solvent, with (2-fluorophenyl)boronic acid, 23.9 mg, 47% yield.

$^1$H NMR (300 MHz, DMSO-d6) δ 9.44 (s, 1H), 8.08 (br s, 1H), 7.87-7.84 (m, 2H), 7.69 (s, 1H), 7.51-7.29 (m, 6H), 7.14 (s, 1H), 7.04 (d, J=7.6 Hz, 1H), 6.34 (dd, J=5.7, 2.8 Hz, 1H), 6.27 (dd, J=5.7, 2.8 Hz, 1H), 4.15 (dd, J=8.0, 8.0 Hz, 1H), 3.51-3.35 (m, partially overlapped with H2O, 4H), 2.85 (s, 1H), 2.80 (s, 1H), 2.45 (d, J=8.4 Hz, 1H), 2.01 (d, J=7.8 Hz, 1H), 1.92-1.82 (m, 4H), 1.38 (d, J=8.4 Hz, 1H); LRMS (M+H) m/z 513.39.

Example 14

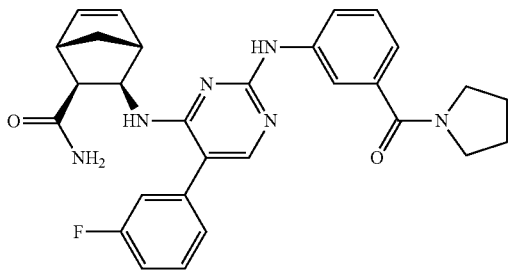 [SMILES: NC(=O)[C@@H]1[C@H](Nc2nc(Nc3cccc(C(=O)N4CCCC4)c3)ncc2-c2cccc(F)c2)[C@H]2C=C[C@@H]1C2]

(1S,2S,3R,4R)-3-((5-(3-fluorophenyl)-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H2O (7:3:2, 3 mL) as solvent, with (3-fluorophenyl)boronic acid, 26 mg, 51% yield.

$^1$H NMR (300 MHz, DMSO-d6) δ 9.37 (s, 1H), 8.01 (br s, 1H), 7.85 (s, 1H), 7.79 (d, br J=8.3 Hz, 1H), 7.66 (s, 1H), 7.50-7.42 (m, 2H), 7.29 (dd, J=7.9, 7.9 Hz, 1H), 7.21-7.12 (m, 4H), 6.98 (d, J=7.4 Hz, 1H), 6.29 (dd, J=5.7, 2.8 Hz, 1H), 6.21 (dd, J=5.7, 2.8 Hz, 1H), 4.16 (dd, J=7.8, 7.8 Hz, 1H), 3.43 (dd, J=6.6, 6.6 Hz, 2H), 3.37-3.30 (m, partially overlapped with H2O, 2H), 2.80 (s, 1H), 2.77 (s, 1H), 2.42 (d, J=8.2 Hz, 1H), 1.96 (d, J=8.2 Hz, 1H), 1.87-1.77 (m, 4H), 1.35 (d, J=8.6 Hz, 1H); LRMS (M+H) m/z 513.48.

Example 15

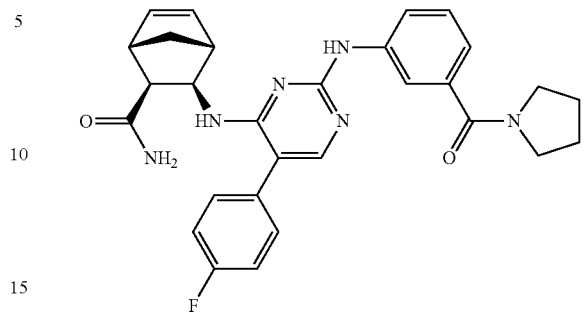

(1S,2S,3R,4R)-3-((5-(4-fluorophenyl)-2-((3-(pyrrolidine-1-carbonyl)phenyl)amino)pyrimidin-4-yl)amino)bicyclo[2.2.1]hept-5-ene-2-carboxamide 0.1 mmol scale, DME-EtOH—H2O (7:3:2, 3 mL) as solvent, with (4-fluorophenyl)boronic acid, 23.3 mg, 45% yield.

$^1$H NMR (300 MHz, DMSO-d6) δ 9.39 (s, 1H), 8.08 (br s, 1H), 7.86-7.83 (m, 2H), 7.72 (s, 1H), 7.46-7.41 (m, 2H), 7.37-7.28 (m, 4H), 7.19 (s, 1H), 7.03 (d, J=7.6 Hz, 1H), 6.34 (dd, J=5.6, 2.8 Hz, 1H), 6.27 (dd, J=5.6, 2.8 Hz, 1H), 4.21 (dd, J=7.5, 7.5 Hz, 1H), 3.49 (dd, J=6.6, 6.7 Hz, 2H), 3.40 (dd, J=6.7, 6.7 Hz, 2H), 2.84 (s, 1H), 2.82 (s, 1H), 2.48 (d, J=8.1 Hz, 1H), 2.00 (d, J=8.7 Hz, 1H), 1.92-1.82 (m, 4H), 1.40 (d, J=8.7 Hz, 1H); LRMS (M+H) m/z 513.34.

Example 16

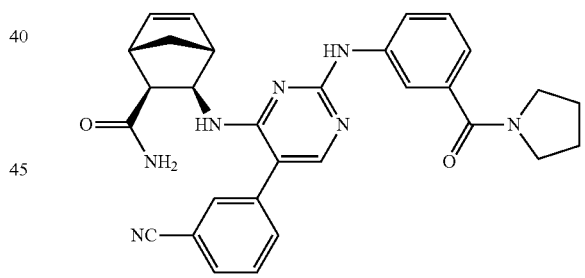

(1S,2S,3R,4R)-3-((5-(3-cyanophenyl)-2-((3-(pyrrolidine-1-carbonyl)phenyl)amino)pyrimidin-4-yl)amino)bicyclo[2.2.1]hept-5-ene-2-carboxamide 0.4 mmol scale, 1,4-dioxane as solvent, with (3-cyanophenyl)boronic acid, 131.3 mg, 63% yield.

$^1$H NMR (300 MHz, DMSO-d6) δ 9.48 (s, 1H), 8.08 (br s, 1H), 7.93 (s, 1H), 7.88-7.83 (m, 3H), 7.77-7.75 (m, 2H), 7.69 (d, J=7.6 Hz, 1H), 7.65-7.61 (m, 1H), 7.36 (dd, J=7.9, 7.9 Hz, 1H), 7.16 (br s, 1H), 7.05 (d, J=7.6 Hz, 1H), 6.35 (dd, J=5.8, 2.9 Hz, 1H), 6.27 (dd, J=5.8, 2.9 Hz, 1H), 4.18 (dd, J=7.8, 7.8 Hz, 1H), 3.49 (dd, J=6.5, 6.5 Hz, 2H), 3.42-3.36 (m, partially overlapped with H2O, 2H), 2.89 (s, 1H), 2.84 (s, 1H), 2.48 (d, J=8.1 Hz, 1H), 2.01 (d, J=8.8 Hz, 1H), 1.93-1.82 (m, 4H), 1.42 (d, J=8.8 Hz, 1H); LRMS (M+H) m/z 520.45.

Example 17

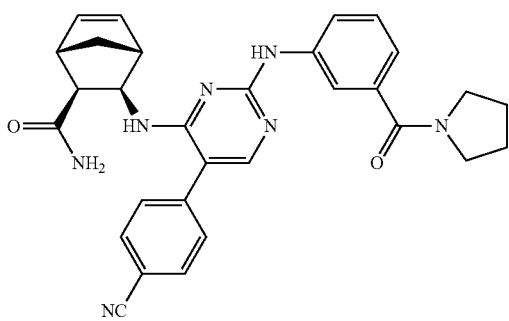 [SMILES: N#Cc1ccc(-c2cnc(Nc3cccc(C(=O)N4CCCC4)c3)nc2N[C@H]2[C@@H](C(N)=O)[C@@H]3C=C[C@H]2C3)cc1]

(1S,2S,3R,4R)-3-((5-(4-cyanophenyl)-2-((3-(pyrrolidine-1-carbonyl)phenyl)amino)pyrimidin-4-yl)amino)bicyclo[2.2.1]hept-5-ene-2-carboxamide 0.4 mmol scale, 1,4-dioxane as solvent, with (4-cyanophenyl)boronic acid, 75.4 mg, 36% yield.

$^1$H NMR (300 MHz, DMSO-d6) δ 9.52 (s, 1H), 8.08 (br s, 1H), 7.95 (s, 1H), 7.92 (d, J=7.7 Hz, 2H), 7.86 (d, J=8.4 Hz, 1H), 7.77 (s, 1H), 7.63 (d, J=8.1 Hz, 2H), 7.56 (d, J=7.5 Hz, 1H), 7.36 (dd, J=7.9, 7.9 Hz, 1H), 7.25 (s, 1H), 7.05 (d, J=7.4 Hz, 1H), 6.35 (dd, J=5.7, 2.8 Hz, 1H), 6.27 (dd, J=5.7, 2.8 Hz, 1H), 4.20 (dd, J=7.7, 7.7 Hz, 1H), 3.49 (dd, J=6.5, 6.5 Hz, 2H), 3.42-3.38 (m, partially overlapped with H2O, 2H), 2.87 (s, 1H), 2.83 (s, 1H), 2.49 (d, J=8.2 Hz, 1H), 2.02 (d, J=8.6 Hz, 1H), 1.92-1.82 (m, 4H), 1.41 (d, J=8.6 Hz, 1H); LRMS (M+H) m/z 520.44.

Example 18

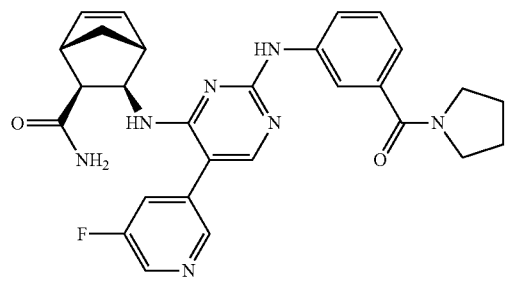 [SMILES: NC(=O)[C@@H]1[C@H](Nc2nc(Nc3cccc(C(=O)N4CCCC4)c3)ncc2-c2cncc(F)c2)[C@H]2C=C[C@@H]1C2]

(1S,2S,3R,4R)-3-((5-(5-fluoropyridin-3-yl)-2-((3-(pyrrolidine-1-carbonyl)phenyl)amino)pyrimidin-4-yl)amino)bicyclo[2.2.1]hept-5-ene-2-carboxamide 0.065 mmol scale, DME-EtOH—H2O (7:3:2, 3 mL) as solvent, with (5-fluoropyridin-3-yl)boronic acid, 14 mg, 42% yield.

$^1$H NMR (300 MHz, DMSO-d6) δ 9.52 (s, 1H), 8.59 (d, J=2.7 Hz, 1H), 8.51 (dd, J=1.7, 1.7 Hz, 1H), 8.09 (br s, 1H), 7.96 (s, 1H), 7.86-7.76 (m, 4H), 7.36 (dd, J=7.9, 7.9 Hz, 1H), 7.23 (s, 1H), 7.05 (d, J=7.5 Hz, 1H), 6.35 (dd, J=5.6, 2.8 Hz, 1H), 6.27 (dd, J=5.6, 2.8 Hz, 1H), 4.17 (dd, J=7.7, 7.7 Hz, 1H), 3.49 (dd, J=6.5, 6.5 Hz, 2H), 3.42-3.36 (m, partially overlapped with H2O, 2H), 2.89 (s, 1H), 2.84 (s, 1H), 2.48 (d, J=7.9 Hz, 1H), 2.00 (d, J=8.7 Hz, 1H), 1.92-1.82 (m, 4H), 1.41 (d, J=8.7 Hz, 1H); LRMS (M+H) m/z 514.34.

Example 19

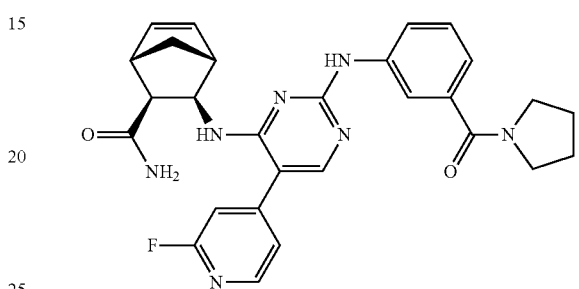

(1S,2S,3R,4R)-3-((5-(2-fluoropyridin-4-yl)-2-((3-(pyrrolidine-1-carbonyl)phenyl)amino)pyrimidin-4-yl)amino)bicyclo[2.2.1]hept-5-ene-2-carboxamide 0.065 mmol scale, DME-EtOH—H2O (7:3:2, 3 mL) as solvent, with (2-fluoropyridin-4-yl)boronic acid, 6 mg, 18% yield.

$^1$H NMR (300 MHz, DMSO-d6) δ 9.60 (s, 1H), 8.30 (d, J=5.2 Hz, 1H), 8.09-8.07 (m, 1H), 8.07 (s, 1H), 7.86-7.78 (m, 3H), 7.43 (ddd, J=5.4, 1.6, 1.6 Hz, 1H), 7.37 (dd, J=7.9, 7.9 z Hz, 1H), 7.27-7.25 (m, 2H), 7.07 (br d, J=7.5 Hz, 1H), 6.36 (dd, J=5.5, 2.8 Hz, 1H), 6.27 (dd, J=5.5, 2.8 Hz, 1H), 4.20 (dd, J=7.1, 7.1 Hz, 1H), 3.49 (dd, J=6.6, 6.6 Hz, 2H), 3.43-3.36 (m, partially overlapped with H2O, 2H), 2.89 (s, 1H), 2.86 (s, 1H), 2.52-2.49 (m, partially overlapped with DMSO, 2H), 2.05 (d, J=8.2 Hz, 1H), 1.93-1.83 (m, 4H), 1.43 (d, J=9.0 Hz, 1H); LRMS (M+H) m/z 514.38.

Example 20

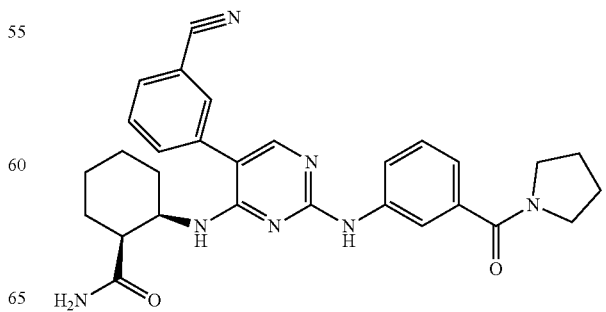

(1S,2R)-2-((5-(3-cyanophenyl)-2-((3-(pyrrolidine-1-carbonyl)phenyl)amino)pyrimidin-4-yl)amino)cyclohexane-1-carboxamide Example 21

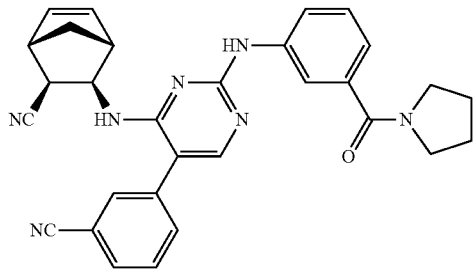 [SMILES: N#Cc1cccc(-c2cnc(Nc3cccc(C(=O)N4CCCC4)c3)nc2N[C@H]2[C@@H](C#N)[C@@H]3C=C[C@H]2C3)c1]

(1S,2 S,3R,4R)-3-((5-(3-cyanophenyl)-2-((3-(pyrrolidine-1-carbonyl)phenyl)amino)pyrimidin-4-yl)amino)bicyclo[2.2.1]hept-5-ene-2-carbonitrile ¹H NMR (300 MHz, DMSO-d6) δ 9.44 (s, 1H), 8.01 (br s, 1H), 7.93-7.91 (m, 2H), 7.86 (ddd, J=7.6, 1.5, 1.5 Hz, 1H), 7.83-7.77 (m, 2H), 7.69 (dd, J=7.7, 7.7 Hz, 1H), 7.37 (dd, J=7.9, 7.9 Hz, 1H), 7.06 (br d, J=7.5 Hz, 1H), 6.92 (d, J=6.7 Hz, 1H), 6.46 (dd, J=5.7, 3.1 Hz, 1H), 6.38 (dd, J=5.7, 2.7 Hz, 1H), 4.21-4.17 (m, 1H), 3.52-3.48 (m, 2H), 3.42-3.29 (m, overlapped with H2O, 3H), 3.23 (s, 1H), 3.03 (s, 1H), 1.95-1.79 (m, 4H), 1.70 (d, J=9.1 Hz, 1H), 1.56 (d, J=9.1 Hz, 1H); LRMS (M+H) m/z 502.55.

Example 22

Intermediate:

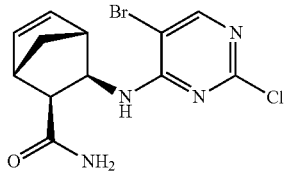 [SMILES: NC(=O)[C@@H]1[C@H](Nc2nc(Cl)ncc2Br)[C@H]2C=C[C@@H]1C2]

(1S,2S,3R,4R)-3-((5-bromo-2-chloropyrimidin-4-yl)amino)bicyclo[2.2.1]hept-5-ene-2-carboxamide ¹H NMR (300 MHz, DMSO-d6) δ 8.58 (d, J=7.6 Hz, 1H), 8.31 (s, 1H), 7.90 (s, 1H), 7.35 (s, 1H), 6.38 (dd, J=5.7, 2.8 Hz, 1H), 6.33 (dd, J=5.7, 2.8 Hz, 1H), 4.04 (dd, J=6.7, 6.7 Hz, 1H), 2.92 (s, 1H), 2.77 (s, 1H), 2.55-2.53 (m, overlapped with DMSO, 1H), 2.08 (d, J=8.7 Hz, 1H), 1.44 (d, J=9.1 Hz, 1H); LRMS (M+H) m/z 344.97.

¹H NMR (300 MHz, Chloroform-d) δ 8.09 (s, 1H), 7.43 (d, J=8.9 Hz, 1H), 6.34 (dd, J=5.7, 3.0 Hz, 1H), 6.28 (dd, J=5.7, 3.0 Hz, 1H), 5.60 (s, 1H), 5.38 (s, 1H), 4.34 (ddd, J=8.4, 8.4, 1.6 Hz, 1H), 3.05 (s, 1H), 2.84 (s, 1H), 2.48 (dd, J=8.0, 1.3 Hz, 1H), 2.21 (ddd, J=9.4, 1.6, 1.6 Hz, 1H), 1.62 (ddd, J=9.4, 1.6, 1.6 Hz, 1H); LRMS (M+H) m/z 345.03.

Example 23

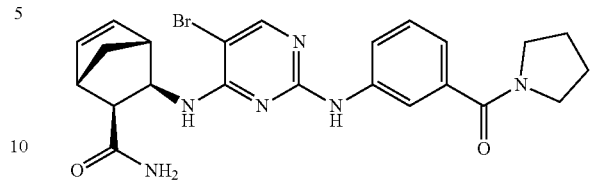

(1S,2S,3R,4R)-3-((5-bromo-2-((3-(pyrrolidine-1-carbonyl)phenyl)amino)pyrimidin-4-yl)amino)bicyclo[2.2.1]hept-5-ene-2-carboxamide ¹H NMR (300 MHz, DMSO-d6) δ 9.48 (s, 1H), 8.09 (br s, 1H), 8.00-7.99 (m, 1H), 7.89-7.86 (m, 2H), 7.78 (br d, J=8.7 Hz, 1H), 7.37-7.31 (m, 2H), 7.05 (dt, J=7.6, 1.3 Hz, 1H), 6.37 (dd, J=5.7, 3.0 Hz, 1H), 6.27 (dd, J=5.7, 3.0 Hz, 1H), 4.14-4.08 (m, 1H), 3.51-3.46 (m, 2H), 3.41-3.36 (m, 2H), 2.91 (s, 1H), 2.81 (s, 1H), 2.55-2.53 (m, overlapped with DMSO, 1H), 2.13 (d, J=8.8 Hz, 1H), 1.92-1.81 (m, 4H), 1.44 (d, J=8.8 Hz, 1H); LRMS (M+H) m/z 497.23, 499.50.

Example 24

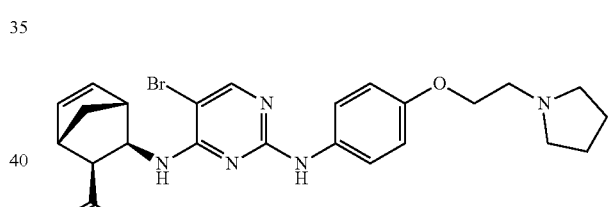

(1S,2 S,3R,4R)-3-((5-bromo-2-((4-(2-(pyrrolidin-1-yl)ethoxy)phenyl)amino)pyrimidin-4-yl)amino)bicyclo[2.2.1]hept-5-ene-2-carboxamide ¹H NMR (300 MHz, DMSO-d6) δ 9.14 (s, 1H), 8.02 (s, 1H), 7.82 (br s, 1H), 7.74 (d, J=7.6 Hz, 1H), 7.64 (d, J=9.1 Hz, 2H), 7.30 (s, 1H), 6.89 (d, J=9.1 Hz, 2H), 6.39 (dd, J=5.6, 2.8 Hz, 1H), 6.35 (dd, J=5.7, 2.9 Hz, 1H), 4.13-4.06 (m, 3H), 2.91 (s, 1H), 2.88-2.83 (m, 2H), 2.82 (s, 1H), 2.65-2.55 (m, partially overlapped with DMSO, 5H), 2.13 (d, J=8.6 Hz, 1H), 1.76-1.72 (m, 4H), 1.44 (d, J=8.6 Hz, 1H); LRMS (M+H) m/z 515.10.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound having a formula 1

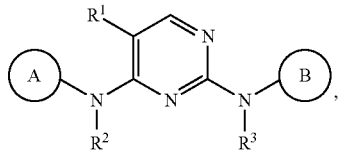

Formula 1 or salt thereof, wherein:
ring A is a carboxamide substituted (C6-C12) cycloalkyl, (C6-C12) cycloalkenyl, (C6-C12) bicycloalkyl or a (C6-C12) bicycloalkenyl ring;
ring B is aryl;
R¹ is (C4-C10)alkyl, (C4-C10)cycloalkyl, aryl, or heteroaryl, wherein if R¹ is pyridinyl then the A ring is other than cyclohexyl; and
R² and R³ are independently hydrogen or (C1-C6)alkyl.

2. The compound according to claim 1, wherein cycloaliphatic ring A is substituted with —CONH₂.

3. The compound according to claim 1, wherein ring B is a mono-, di- or tri-substituted phenyl ring.

4. The compound according to claim 1, wherein ring B is substituted with a substituent selected from (C1-10)amide, (C3-C10)cycloamide, (C1-C10)alkyl, (C1-C10)alkoxyl, (C3-C10)cycloalkoxyl, halo, (C3-C10)cycloalkyl or (C3-C10)heterocycloalkyl.

5. The compound according to claim 4, wherein the substituent is methyl or fluoro.

6. The compound according to claim 1, wherein the A ring is selected from

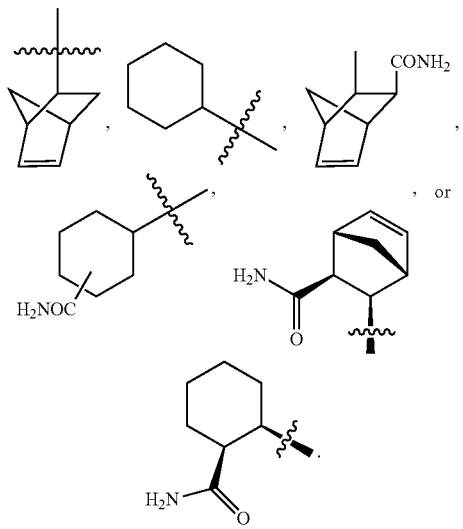

7. The compound according to claim 1, wherein the B ring is selected from

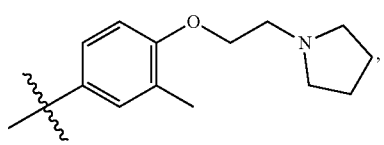

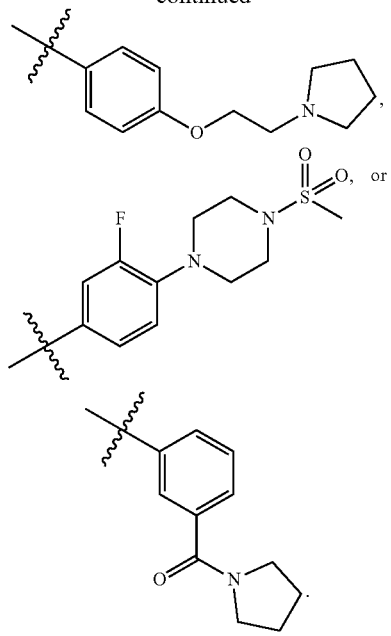

8. The compound according to claim 1, wherein R¹ is aryl or heteroaryl.

9. A compound, having a formula

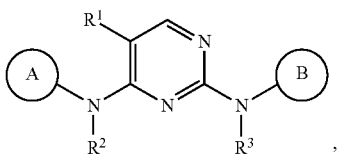

Formula 1 or salt thereof, wherein:
ring A is cycloaliphatic;
ring B is aryl;
R¹ is

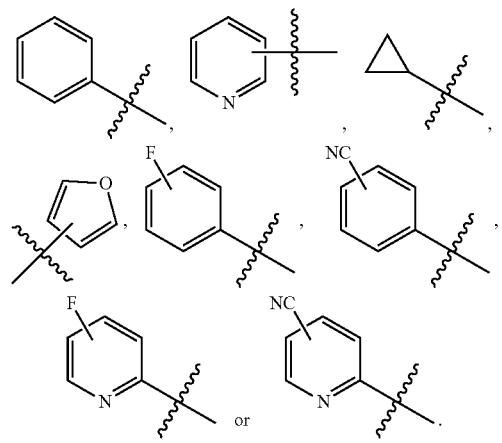

and
R² and R³ are independently hydrogen or (C1-C6)alkyl.

10. The compounds according to claim 1, having a formula selected from

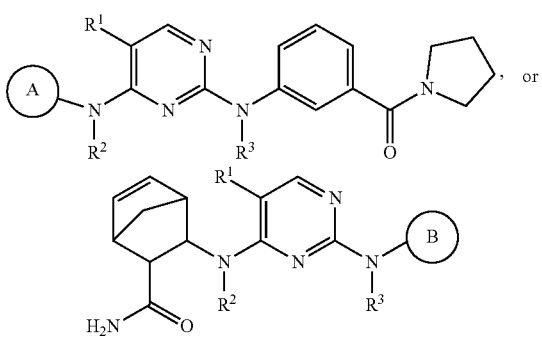

wherein the A ring, the B ring, $R^1$, $R^2$ and $R^3$ are as stated in claim 1.

11. A compound, having a formula

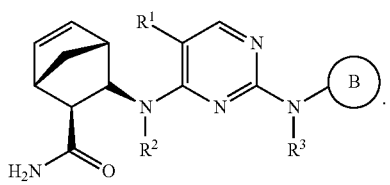

wherein:
  ring B is aryl;
  $R^1$ is (C1-C10)alkyl, (C3-C10)cycloalkyl, aryl, or heteroaryl; and
  $R^2$ and $R^3$ are independently hydrogen or (C1-C6)alkyl.

12. A compound, having a formula selected from

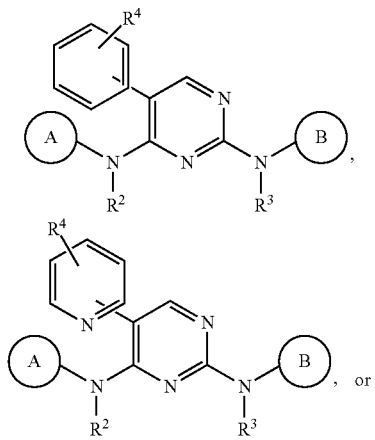

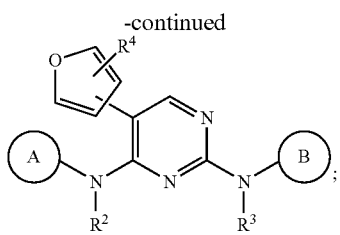

wherein:
  the A ring is cycloaliphatic;
  the B ring is aryl;
  $R^2$ and $R^3$ are independently hydrogen or (C1-C6)alkyl; and
  $R^4$ is selected from (C1-C6)alkyl, cyano, halo and hydrogen.

13. The compound according to claim 12, wherein $R^4$ is methyl or fluoro.

14. The compound according to claim 1, having a formula selected from

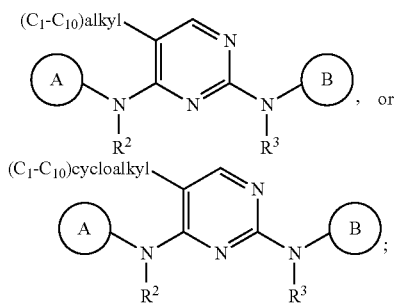

wherein the A ring, the B ring, and $R^2$ and $R^3$ are as stated in claim 1.

15. A pharmaceutical composition comprising a compound according to claim 1 and a pharmaceutically acceptable excipient.

16. A method for inhibiting a protein, comprising contacting an IRAK or TAK protein with an effective amount of a compound of claim 1.

17. The method according to claim 16, comprising administering to a subject in need thereof an effective amount of a compound of claim 1.

18. The method according to claim 16, wherein the IRAK protein is IRAK4, and the TAK protein is TAK1.

* * * * *